United States Patent [19]

*Johs et al.

[11] Patent Number: 5,872,630
[45] Date of Patent: Feb. 16, 1999

[54] REGRESSION CALIBRATED SPECTROSCOPIC ROTATING COMPENSATOR ELLIPSOMETER SYSTEM WITH PHOTO ARRAY DETECTOR

[76] Inventors: Blaine D. Johs, 5317 NW 6th St., Lincoln, Nebr. 68521; Daniel W. Thompson, 5301 London Rd., Lincoln, Nebr. 68516

[*] Notice: The term of this patent shall not extend beyond the expiration date of Pat. No. 5,666,201.

[21] Appl. No.: 912,211

[22] Filed: Aug. 15, 1997

Related U.S. Application Data

[63] Continuation-in-part of Ser. No. 530,892, Sep. 20, 1995, Pat. No. 5,666,201, and a continuation-in-part of Ser. No. 618,820, Mar. 20, 1996, Pat. No. 5,706,212.

[51] Int. Cl.$^6$ .................................................. G01N 21/21
[52] U.S. Cl. .......................... 356/369; 364/525; 250/225
[58] Field of Search ..................................... 356/369, 365, 356/364, 366, 367, 368; 250/225

[56] References Cited

U.S. PATENT DOCUMENTS

| | | | |
|---|---|---|---|
| 4,053,232 | 10/1977 | Dill et al. | 356/118 |
| 4,668,086 | 5/1987 | Redner | 356/33 |
| 5,329,357 | 7/1994 | Bernoux et al. | 356/369 |
| 5,373,359 | 12/1994 | Woolan et al. | 356/328 |
| 5,504,582 | 4/1996 | Johs et al. | 356/369 |
| 5,521,706 | 5/1996 | Green et al. | 356/369 |
| 5,581,350 | 12/1996 | Chen et al. | 356/369 |
| 5,596,406 | 1/1997 | Rosencwaig et al. | 356/327 |
| 5,666,201 | 9/1997 | Johs et al. | 356/369 |
| 5,706,212 | 1/1998 | Thompson et al. | 356/367 |
| 5,757,494 | 5/1998 | Green et al. | 356/369 |

OTHER PUBLICATIONS

Regression Calibration Method for Rototins Elknent Ellipoimeter Johs, Thin Solid Films 234 (1993).
System aTic Errors on Rotating—Compensator Ellipionetry, hleim et al., J. Opt. Am. A/vol. 11, No. 9, 1994.
Waveform Analysis Withoptical Multichannel Detectors—An & Collins, Rev. Sci. Instrum 62(8) 1991.
Extension of Rotating–Analyzo–Elliprometry To Generalized Ellio—Schubert et al., J. Opt. Soc. Am. A., 13, 1996.
Polarization Dependent Parameters of Arbitrary Anisotrapil—Schubert, Phys. Rev. B, 53, 1996.
Generalized Transmission ellipsometry for Twisted Biaxial—Schubert et al., J. Opt. Soc. Am. A/vol. 13, No. 9, 1996.
Automated Rotating Element Ellipsometer: Calibration, operation—Collins, Rev. Sci. Instrum. 61(8), 1990.
Oriel Data Sheets for Quarzo Mica Petorders.
Meadow lautz optics Data Sheets for feso order Retorders.
Meadow lautz optics Data Sheets for Achromatic Retorders.
Nev focus Data Sheet for Berck–Type Retorders.
The Berek Polorization Compensator, model 5540 user's manual, by new Focus.

*Primary Examiner*—Hoa Q. Pham
*Attorney, Agent, or Firm*—James D. Welch

[57] ABSTRACT

A Spectroscopic Rotating Compensator Material System Investigation System including a Photo Array for simultaneously detecting a Multiplicity of Wavelengths is disclosed. The Spectroscopic Rotating Compensator Material System Investigation System is calibrated by a Mathematical Regression based technique involving, where desirable, Parameterization of Calibration Parameters. Calibration is possible utilizing a single two dimensional Data Set obtained with the Spectroscopic Rotating Compensator Material System Investigation System in a "Material System present" or in a Straight-through" configuration.

43 Claims, 22 Drawing Sheets

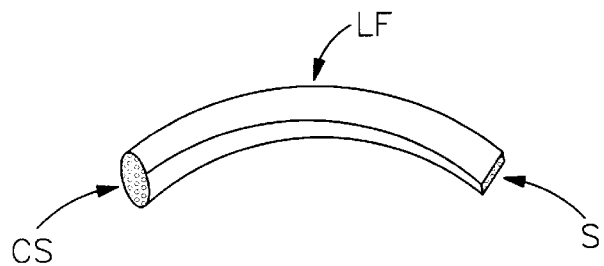
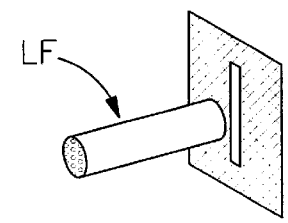
FIG. 9a       FIG. 9b
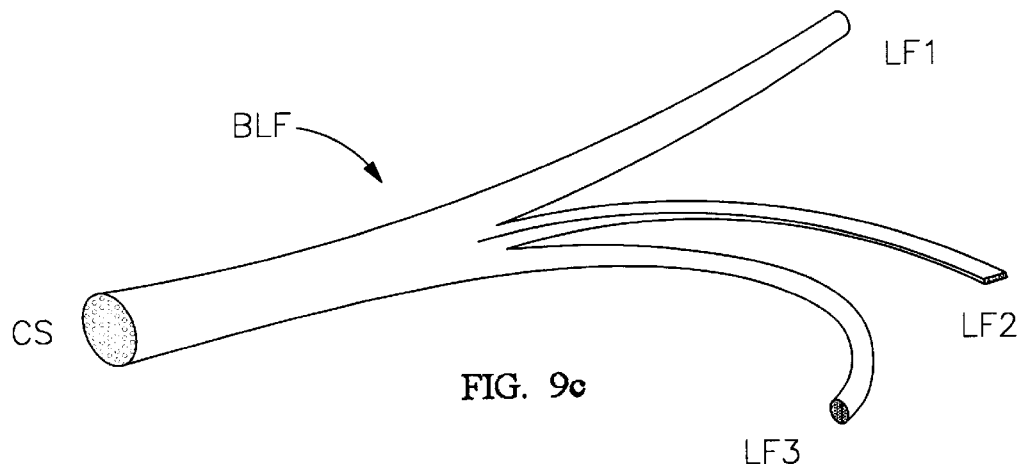
FIG. 9c
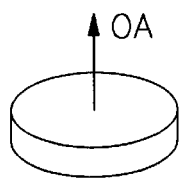  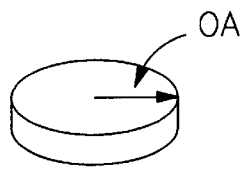  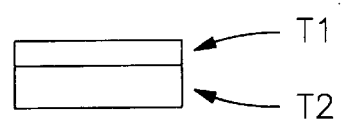
FIG. 9d       FIG. 9e       FIG. 9f

REGRESSION CALIBRATED SPECTROSCOPIC ROTATING COMPENSATOR ELLIPSOMETER SYSTEM WITH PHOTO ARRAY DETECTOR

This application is a Continuation-In-Part of application Ser. No. 08/530,892 filed Sep. 20, 1995, now U.S. Pat. No. 5,666,201, and of application Ser. No. 08/618,820 filed Mar. 20, 1996, now U.S. Pat. No. 5,706,212. This application is further a Continuation-In-Part of now abandoned Provisional Applications Serial Nos. 60/039,519 and 60/042,661 filed on Mar. 03, 1997 and Apr. 04, 1997 respectively.

TECHNICAL FIELD

The present invention relates to ellipsometers and polarimeters and the like, and more particularly is a Spectroscopic Rotating Compensator Material System Investigation System including a Photo Array for simultaneously detecting a Multiplicity of Wavelengths, which Spectroscopic Rotating Compensator Material System Investigation System is calibrated by a Mathematical Regression based technique involving, where beneficial and desired, Parameterization of Calibration Parameters. The present invention system can be realized utilizing off-the-shelf non-ideal compensators and diode array spectrometers.

BACKGROUND

Ellipsometry is a well known means by which to monitor material systems. In brief, a polarized beam of electromagnetic radiation of one or more wavelengths is caused to impinge upon a materials system along one or more angles of incidence and then interact with a material system. Beams of electromagnetic radiation can be considered as comprised of two orthogonal components, (ie. "P" and "S"), where "P" identifies a plane which contains both an incident beam of electromagnetic radiation, and a normal to an investigated surface of a material system being investigated, and where "S" identifies a plane perpendicular to the "P" plane and parallel to said surface of said material system. A change in polarization state in a polarized beam of electromagnetic radiation caused by said interaction with a material system, is representative of properties of said material system. (Note Polarization State basically refers to a magnitude of a ratio of orthogonal component magnitudes in a polarized beam of electromagnetic radiation, and a phase angle therebetween.) Generally two well known angles, (PSI and DELTA), which characterize a material system at a given Angle-of-Incidence, are determined by analysis of data which represents change in polarization state.

Continuing, Ellipsometer Systems generally include a source of a beam of electromagnetic radiation, a Polarizer, which serves to impose a linear state of polarization on a beam of electromagnetic radiation, a Stage for supporting a sample system, and an Analyzer which serves to select a polarization state in a beam of electromagnetic radiation after it has interacted with a material system, and pass it to a Detector System for analysis therein. As well, one or more Compensator(s) can be present and serve to affect a phase angle between orthogonal components of a polarized beam of electromagnetic radiation.

A number of types of ellipsometer systems exist, such as those which include rotating elements and those which include modulation elements. Those including rotating elements include Rotating Polarizer (RP), Rotating Analyzer (RA) and Rotating Compensator (RC). The present invention is, in its primary embodiment, a Rotating Compensator Ellipsometer System. It is noted that Rotating Compensator Ellipsometer Systems do not demonstrate "Dead-Spots" where obtaining data is difficult. They can read PSI and DELTA of a Material System over a full Range of Degrees with the only limitation being that if PSI becomes essentially zero (0.0), one can't then determine DELTA as there is not sufficient PSI Polar Vector Length to form the angle between the PSI Vector and an "X" axis. In comparison, Rotating Analyzer and Rotating Polarizer Ellipsometers have "Dead Spots" at DELTA's near 0.0 or 180 Degrees and Modulation Element Ellipsometers also have "Dead Spots" at PSI near 45 Degrees). The utility of Rotating Compensator Ellipsometer Systems should then be apparent. Another benefit provided by fixed Polarizer (P) and Analyzer (A) positions is that polarization state sensitivity to input and output optics during data acquisition is essentially non-existent. This enables relatively easy use of optic fibers, mirrors, lenses etc. for input/output.

A Search of Patents relevant to the present invention has identified very little. One Patent, to Dill, U.S. Pat. No. 4,053,232 describes a Rotating-Compensator Ellipsometer System, which operates utilizes monochromatic light. Two Patents which identify systems which utilize Polychromatic light in investigation of material systems are described in U.S. Pat. Nos. 5,596,406 and 4,668,086, to Rosencwaig et al. and Redner, respectively, were also identified. Also identified is a Patent to Woollam et al. U.S. Pat. No. 5,373,359 as it describes a Rotating Analyzer Ellipsometer System which utilizes white light. Patents continued from the 359 Woollam et al. Patent are, U.S. Pat. Nos. 5,504,582 to Johs et al. and 5,521,706 to Green et al. Said 582 Johs et al. and 706 Green et al. Patents describe use of polychromatic light in a Rotating Analyzer Ellipsometer System. A Patent to Bernoux et al., U.S. Pat. No. 5,329,357 is identified as it describes the use of optical fibers as input and output means in an ellipsometer system. A Patent to Chen et al., U.S. Pat. No. 5,581,350 is identified as it describes the application of regression in calibration of ellipsometer systems. An article by Johs, titled "Regression Calibration Method For Rotating Element Ellipsometers", which appeared in Thin Film Solids, Vol. 234 in 1993 is also identified as it predates the Chen et al. Patent and describes an essentially similar approach to ellipsometer calibration. An article by Jellison Jr. titled "Data Analysis for Spectroscopic Ellipsometry", Thin Film Solids, 234, (1993) is identified as it describes a method fo determining the accuracy with which certain data points can be measured, which information allows adding a weighting factor to a curve fitting regression procedure as applied to a multiplicity of data points, said weighting factor serving to emphasize the effect of mot accurate and precise data. A book by Azzam and Bashara titled "Ellipsometry and Polarized light" North-Holland, 1977 is disclosed and incorporated herein by reference for general theory. An article by Collins titled "Automated Rotating Element Ellipsometers: Calibration, Operation, and Real-Time Applications", Rev. Sci. Instrum. 61(8), August 1990 is identified as it provides insight into rotating element ellipsometers. An article by Kleim et al. titled "Systematic Errors in Rotating-Compensator Ellipsometry" published in J. Opt. Soc. Am./Vol. 11, No. 9, Sept 1994 is identified as it describes calibration of rotating compensator ellipsometers. An Article by An and Collins titled "Waveform Analysis With Optical Multichannel Detectors: Applications for Rapid-Scan Spectroscopic Ellipsometer", Rev. Sci. Instrum., 62 (8), August 1991 is also identified as it discusses effects such as Detection System Error Characterization, Stray Light, Image Persistence etc., and calibration thereof. Also disclosed are articles by Schubert et al. which describe "Generalized Ellipsometry". The first thereof is titled "Extension Of Rotating-Analyzer Ellipsometry To Generalized Ellipsometry: Determination Of The Dielectric Function Tensor From Uniaxial TiO2", J. Opt. Soc. Am. A. 13, (1996). The second such article is authored by M. Schubert alone and is titled "Polarization Dependent Parameters Of Arbitrary Anisotropic Homogeneous Epitaxial Systems", Phys. Rev. B 53, (1996). The third such article is titled "Generalized Transmission Ellipsometry For Twisted Biaxial Dielectric Media: Application To Chiral Liquid Crystals", J. Opt. Soc. Am. A/Vol. 13, No. 9 (1996). Further identified for authority regarding regression is a book titled Numerical Recipes in "C", 1988, Cambridge University Press.

In view of the foregoing, a need remains for a Spectroscopic Rotating Compensator Material System Investigation System, including a Photo Array, for simultaneously detecting a Multiplicity of Wavelengths, which Spectroscopic Rotating Compensator Material System Investigation System can be operated with essentially any Achromatic or non-Achromatic Compensator.

DISCLOSURE OF THE INVENTION

It is generally considered that while Rotating Compensator Material System Investigation Systems, (eg. Rotating Compensator Ellipsometers), provide many benefits, (eg. Material System PSI and DELTA investigation limiting "dead-spots" are not present), that in the absence of essentially Achromatic "ideal" Compensators it would be prohibitively difficult and expensive to build, calibrate and utilize a "Spectroscopic" Rotating Compensator Material System Investigating System. This is to be understood in light of the fact that Compensators which are essentially Achromatic, (ie. provide essentially constant retardation over a large range of Wavelengths, such as 190–1000 nanometers), are not generally and economically available as off-the-shelf items.

The present invention system is, however, an affordable, easy to calibrate and utilize Spectroscopic Rotating Compensator Material System Investigation System comprising a Source of a Polychromatic Beam of Electromagnetic Radiation, a Polarizer, a Stage for Supporting a Material System, an Analyzer, a Dispersive Optics and at least one Photo Array Detector Element System which contains a multiplicity of Detector Elements, which Spectroscopic Rotating Compensator Material System Investigation System further comprises at least one Compensator(s) positioned at a location selected from the group consisting of: (before said stage for supporting a sample system and after said stage for supporting a sample system and both before and after said stage for supporting a sample system).

Of particular importance is the fact that said at least one Compensator(s) utilized in the present invention can be essentially any available, reasonably priced, off-the-shelf Retardation providing system, including non-Achromatic, Berek-type, Zero-Order Waveplate, Multiple-Order Waveplate, Combinations of Multiple-Order Waveplates, Polymer Retarder, Mica Waveplate, Freshnel Rhomb, Achromatic, and Pseudo-Achromatic, etc.

For general information, it is noted that a Berek-type Compensator is a uniaxially anisotropic plate of material in which the Optical Axis is oriented perpendicularly to a plate surface thereof. When a Polarized Beam of Electromagnetic Radiation is caused to be incident other than along the Optical Axis, orthogonal components thereof encounter different effective Indicies of Refraction, thereby effecting retardation therebetween. A Zero-Order Quartz Waveplate is typically constructed by combining two Multi-Order (Quartz) Waveplates which have Optical Axes oriented at ninety (90) degrees with respect to one another. The two Multi-Order waveplates are selected so that the difference in retardation entered by each gives rise to an overall Zero-Order retardance characteristic. Polymer Compensators are made of a polymer material and can provide true Zero-Order retardance which, as do many Compensators, provides an inverse wavelength functional Retardance Characteristic. Essentially Achromatic (Pseudo-Achromatic) Compensators can be constructed by stacking appropriately chosen Polymer and Crystal waveplates. A potential advantage of said essentially Achromatic Compensators is that Retardance can be essentially constant over a range of wavelengths.

While it is known that generally available Compensators do not provide an exact Ninety (90) Degrees of Retardation at all wavelengths over a relatively large range of Wavelengths, the present invention, as described supra herein, utilizes a Regression based Calibration procedure which compensates for said non-ideal Compensator Retardation characteristics. And while it is true that the sensitivity and accuracy of a Rotating Compensator Material System Investigation System degrades as the Retardance provided by a utilized Compensator approaches zero (0.0) or one-hundred-eighty (180) degrees, it has been found that Compensators which demonstrate Retardation, over a range of utilized Wavelengths, of from forty (40) to one-hundred-seventy (170) degrees, are acceptable for use in the present invention, and allow achieving very impressive results over a demonstrated relatively large range of wavelengths, (eg. at least two-hundred-fifty (250) to one-thousand (1000) nanometers).

When the present invention Spectroscopic Rotating Compensator Material System Investigation System is used to investigate a Material System present on said Stage for Supporting a Material System, said Analyzer and Polarizer are maintained essentially fixed in position and at least one of said at least one Compensator(s) is/are caused to continuously rotate while a Polychromatic Beam of Electromagnetic Radiation produced by said Source of a Polychromatic Beam of Electromagnetic Radiation is caused to pass through said Polarizer and said Compensator(s). Said Polychromatic Beam of Electromagnetic Radiation is also caused to interact with said Material System, pass through said Analyzer and interact with said Dispersive Optics such that a Multiplicity of Essentially Single Wavelengths are caused to simultaneously enter a corresponding multiplicity of Detector Elements in said Detector System Photo Array.

A method of calibrating a present invention Spectroscopic Rotating Compensator Material System Investigation System can comprise the steps of:

a. providing a present invention Spectroscopic Rotating Compensator Material System Investigation System as just described infra herein.

b. developing a Mathematical Model of said Spectroscopic Rotating Compensator Material System Investigation System which comprises as Calibration Parameter variables Polarizer Azimuthal Angle Orientation, present Material System PSI, present Material System DELTA, Compensator Azimuthal Angle Orientation(s), Matrix Components of said Compensator(s), Analyzer Azimuthal Angle Orientation, and optionally Detector Element Image Persistance and Readout non-Idealities, which Mathematical Model is effectively a Transfer Function which enables calculation of Electromagnetic Beam Intensity as a function of Wavelength detected by a Detector Element, given Intensity as a function of wavelength provided by said Source of a Polychromatic Beam of Electromagnetic Radiation, said Mathematical Model optionally providing equations for Coefficients of Terms in said Transfer Function, said Coefficients of terms being functions of Calibration Parameters;

c. causing a Polychromatic Beam of Electromagnetic Radiation produced by said Source of a Polychromatic Beam of Electromagnetic Radiation, to pass through said Polarizer, interact with a Material System caused to be in the path thereof, pass through said Analyzer, and interact with said Dispersive Optics such that a Multiplicity of Essentially Single Wavelengths are caused to simultaneously enter a corresponding Multiplicity of Detector Elements in said at least one Detector System, with said Polychromatic Beam of Electromagnetic Radiation also being caused to pass through said Compensator(s) positioned at a location selected from the group consisting of: (before said Stage for Supporting a Material System and after said Stage for Supporting a Material system and both before and after said Stage for Supporting a Sample System);

d. obtaining an at least Two Dimensional Data Set of Intensity Values vs. Wavelength and a parameter selected from the group consisting of: (Angle-Of-Incidence of said Polychromatic Beam of Electromagnetic Radiation with respect to a present Material System, and Azimuthal Angle Rotation of one element selected from the group consisting of: (said Polarizer and said Analyzer)), over time, while at least one of said at least one Compensator(s) is caused to continuously rotate and, optionally, from said data set calculating numerical values for Coefficients of Terms in the Transfer Function for said Spectroscopic Rotating Compensator Material System Investigation System;

e. performing a Mathematical Regression of said Mathematical Model onto said at least Two Dimensional Data Set and/or onto values for Coefficients of Terms in the Transfer Function to evaluate said Calibration Parameters;

said Regression based Calibration Procedure evaluated Calibration Parameters serving to compensate said Mathematical Model for non-Achromatic characteristics and non-Idealities of said Compensator(s), and for Azimuthal Angle Orientations of said Polarizer, Analyzer and Compensator(s).

In addition, evaluation of Detector System Detector Element Image Persistance and Readout non-Ideality compensation Calibration Parameters also included in the Mathematical Model, can simultaneously be carried out in the Mathematical Regression Procedure.

It is noted that where two Compensators are present, each can be rotated at essentially the same, or different speeds.

Said Method of Calibrating a Spectroscopic Rotating Compensator Material System Investigation System can include, in the step of providing the Dispersive Optics and Photo Array Detector Elements of the Spectroscopic Rotating Compensator Material System Investigation System, the step of effecting common mounting thereof with a Beam Splitting Means, said Beam Splitting Means serving to divert a portion of the Polychromatic Beam of Electromagnetic Radiation which otherwise proceeds to said Dispersive Optics, and transmit the remainder of said Polychromatic Beam of Electromagnetic Radiation toward said Dispersive Optics. In use, the diverted portion of said Polychromatic Beam of Electromagnetic Radiation can then be directed by said Beam Splitting Means into an Alignment Means, (which can be a Cross-Hairs or an Automated Polychromatic Beam of Electromagnetic Radiation Detecting and commonly mounted Dispersive Optics and Detector Elements Orientation Control Means). In use said Alignment Means then provides monitored Alignment Capability thereby allowing precise control of the Locus of Propagation of the portion of said Polychromatic Beam of Electromagnetic Radiation which passes through said Beam Splitting Means, interacts with said Dispersive Optics, and enters said Detector Elements.

Said Method of Calibrating a Spectroscopic Rotating Compensator Material System Investigation System can also include, in the step of providing a Mathematical Model, the steps of providing a Matrix Representation of each of said Polarizer, present Material System, said Compensator (s), and said Analyzer, and determining a Mathematical Transfer Function relating Electromagnetic Beam Intensity Out to Intensity In, as a function of Wavelength, by multiplication of said Matrices in a Spectroscopic Rotating Compensator Material System Investigation System element presence representing order.

Said Method of Calibrating a Spectroscopic Rotating Compensator Material System Investigation System can involve, in the step of calculating values of Coefficients of a Transfer Function from said Data Set, the calculation of values of Coefficients of a Fourier Series, (eg. $\alpha_2$, $\alpha_4$, $\beta_2$, $\beta_4$, in Eqs. 11–14 supra).

Additionally, said Method of Calibrating a Spectroscopic Rotating Compensator Material System Investigation system can further comprise the step of Parameterizing Calibration Parameters by representing variation as a function of Wavelength, (or perhaps Angle-Of-Incidence of said Polychromatic Beam of Electromagnetic Radiation with respect to a Surface of an Investigated Material System or Other Variable), by a Calibration Parameter containing Mathematical Equation, Calibration Parameter(s) in said Calibration Parameter containing Mathematical Equation being evaluated during said Mathematical Regression. (See Eqs. 51 & 52 supra). When this is done the Calibration Parameter containing Mathematical Equation provides a functional relationship, and, it is noted, can even be a constant value over a range of, for instance, Wavelenghts, (eg. Polarizer Azimuthal Angle setting). (Note, said parametered approach to mathematical regression based calibration parameter evaluation is better described supra herein under the Headings GLOBAL REGRESSION MODES 1, 2 and 3).

It is further noted that the at least Two Dimensional Data Set can be obtained with the Spectroscopic Rotating Compensator Material System Investigation System oriented in a "Straight-Through" or "Material-System-Present" configuration. In the first configuration open atmosphere essentially constitutes a material system, and a Polarized Electromagnetic Beam passes directly through the Polarizer, Compensator(s) and Analyzer into the Detector System. In the second configuration a Material System is present which presents PSI and DELTA values other than those of the open atmosphere so that a Polychromatic Electromagnetic Beam passes through the Polarizer, possibly a Compensator, and then interacts with a Material System, before passing through, possibly, a Compensator, an Analyzer and into the Detector System. Compensator(s), it should be understood, can be present before and/or after the Material System.

With the above general description of the present invention System and Calibration Method in mind, attention is directed to providing a detailed demonstration of the Calibration Procedure of the present invention as applied to a Spectroscopic Rotating Compensator Ellipsometer System sequentially comprised of:

A Polychromatic Light Source—A Fixed Polarizer—A Material Sample—A Continuously Rotating Compensator—A Fixed Analyzer—and A Detector Element containing Photo Array.

(Note: the Reflection mode side of FIG. 1 of this Disclosure shows this basic configuration where Compensator (C) is considered as removed and only Compensator (C') remains present).

It is to be appreciated, however, that the basic approach to calibration described directly, is adaptable for use in systems in which the Continuously Rotating Compensator is placed ahead of a Material System, and in systems in which two Compensators are present, one ahead of, and one after a Material System wherein one or both are caused to Continuously Rotate in use. For instance, in the case where a Rotating Compensator is placed ahead of the Material Sample, rather than thereafter, simply exchanging references to Polarizer and Analyzer in equations derived for the case where the Rotating Compensator is placed after the Material System, provides the applicable equations.

Transfer function equations for the Rotating Compensator system configured as recited above can be obtained from multiplication of Matrix Representations of the various components, in an appropriate order, in conjunction with Trig function containing Rotation Matrices, which serve to align coordinate systems between components. Eq. 1 shows said Matrix representation:

$$E(P, \Psi, \Delta, C, r1, r2, r3, r4, A) = \begin{pmatrix} 1 & 0 \\ 0 & 0 \end{pmatrix} \cdot \begin{pmatrix} \cos(A) & \sin(A) \\ -\sin(A) & \cos(A) \end{pmatrix} \cdot \quad (1)$$

$$\begin{pmatrix} \cos(C) & -\sin(C) \\ \sin(C) & \cos(C) \end{pmatrix} \cdot \begin{pmatrix} r1 & r3 \\ r2 & r4 \end{pmatrix} \cdot \begin{pmatrix} \cos(C) & \sin(C) \\ -\sin(C) & \cos(C) \end{pmatrix} \cdot$$

$$\begin{pmatrix} \sin\Psi \cdot e^{1 \cdot \Delta} & 0 \\ 0 & \cos\Psi \end{pmatrix} \cdot \begin{pmatrix} \cos(P) \\ \sin(P) \end{pmatrix}$$

where:

ψ and Δ are the traditional ellipsometric parameters which describe the Material System;

P is the azimuthal orientation of the Polarizer;

C is the azimuthal orientation of the Rotating Compensator;

r1, r2, r3 & r4 are the Jones Matrix elements which describe the Compensator, (Note that a Jones Matrix is utilized, however, a Mueller Matrix or other Matrix could also be utilized);

A is the azimuthal orientation of the Analyzer.

The Light Intensity which is measured by a Detector is provided by multiplying through the Matrices in Eq. 1 to provide a Complex Result, then multiplying said Complex Result by its Complex Conjugate. Eq. 2 indicates this:

$$I(P,\psi,\Delta,C,r1,r2,r3,r4,A) = E(P,\psi,\Delta,C,r1,r2,r3,r4,A) \cdot E^*(P,\psi,\Delta,C,r1,r2,r3,r4,A) \quad (2)$$

The Intensity Equation I(t), (Eq. 8):

$$I(t) = I_o(DC + \alpha_2 \cos 2C + \beta_2 \sin 2C + \alpha_4 \cos 4C + \beta_4 \sin 4C) \quad (8)$$

which results from said multiplication is very involved, but can be expressed in terms of intermediate results as provided in Eqs. 3–7, via Eqs. 9.

$$p1 = \sin\Psi \cdot (\cos\Delta + i \cdot \sin\Delta) \cdot \cos P \quad (3)$$
$$p2 = \cos\Psi \cdot \sin P$$

$$K1 = (-p1 \cdot r3 + p2 \cdot r3) \quad (4)$$
$$K2 = (p1 \cdot r1 + p2 \cdot r3)$$
$$K3 = (-p1 \cdot r4 + p2 \cdot r2)$$
$$K4 = (p1 \cdot r2 + p2 \cdot r4)$$

$$U1 = (\cos(A) \cdot K2 + \sin(A) \cdot K4) \quad (5)$$
$$U2 = (K3 + K2) \cdot \sin(A) + (K1 - K4) \cdot \cos(A)$$
$$U3 = (-\cos(A) \cdot K3 + \sin(A) \cdot K1)$$

$$V1 = U1 \cdot \overline{U1} \quad V2 = U2 \cdot \overline{U2} \quad V3 = U3 \cdot \overline{U3} \quad (6)$$
$$V4 = 2 \cdot Re(U1 \cdot \overline{U2}) \quad V5 = 2 \cdot Re(U1 \cdot \overline{U3}) \quad V6 = 2 \cdot Re(U2 \cdot \overline{U3})$$

$$T1 = V1 + V3 \quad T2 = V2 + V5 \quad T3 = V1 - V3 \quad (7)$$
$$T4 = V4 + V6 \quad T5 = V4 - V6$$

where Eqs. 9 provide that:

$$DC = \frac{3}{8} T1 + \frac{1}{8} \cdot T2 \quad (9)$$
$$\alpha_2 = \frac{1}{2} \cdot T3 \qquad \beta_2 = \frac{1}{4} \cdot T4$$
$$\alpha_4 = \frac{1}{8} \cdot (T1 - T2) \qquad \beta_4 = \frac{1}{8} \cdot T5$$

and C=ω·t, where 'ω' is the angular frequency of the continuously rotating Compensator and $I_o$ is an arbitrary constant.

(It is further noted that Eq. 8 is a truncated Fourier Series, and could include additional, higher harmonic terms).

Equations 1–9 are appropriate for a Material System which does not depolarize an Electromagnetic Beam used to investigate a Material System, such that Jones Matrix formalism is appropriate. If a Material System is investigated which does depolarize an investigation electromagnetic beam, then Mueller Matrix formalism can be substituted. As well, the "Isotropic" Material System Matrix in Eq. 1 could be replaced by a General Material System Matrix in the Rotating Compensator. This is described by M. Schubert in the context of "Generalized Ellipsometry", (see Background Section for citations to relevant articles which treat the topic of Generalized ellipsometry by Schubert).

If an ideal Compensator is assumed, where the Jones Matrix components are:
r1=1;
r2=0;
r3=0; and
r4=$e^{1 \cdot \delta}$;
then the Eqs. 9 become Eqs 10–14:

$DC$=(½) (1+cos δ) [cos 2$A$ (cos 2$P$−cos 2ψ)+sin 2$A$ sin 2$P$ sin 2$T$ cosΔ]−cos 2$A$ cos 2$P$ cos 2ψ+1 (10)

$\alpha_2$=−sin 2$A$ sin 2$P$ sin δ sin Δ (11)

$\beta_2$=cos 2$A$ sin 2$P$ sin δ sin 2ψ sin Δ (12)

$\alpha_4$=(½) (1 −cos δ) [cos 2$A$ (cos 2$P$−cos 2ψ)−sin 2$A$ sin 2$P$ sin 2ψ cosΔ] (13)

$\beta_4$=(½) (1−cos δ) [sin 2$A$ (cos 2$P$−cos 2ψ)+cos 2$A$ sin 2$P$ sin 2ψ cosΔ] (14)

It is noted that said Eqs. 10–14 are found in Kleim et al. as referenced in the Background Section of this Specification, with "A" and "P" interchanged. (The Kleim et al. work assumed a Rotating Compensator present prior to a Material System).

Continuing, Eqs. 10–14 are valid for an ideal Rotating Compensator System wherein the Azimuthal angles of the optics are perfectly aligned with the Material Sample frame of reference. In practice this is never true, and offset terms "A'", "P'" and "C'" must be entered to provide Eqs. 15a and 15b:

$$A=A'-A_s, P=P'-P_s \tag{15a}$$

$$C=C'-C_s \tag{15b}$$

where the A', C' and P' indicate dial readings and the $A_s$, $C_s$ and $P_s$ indicate Offset Angles to be determined by a Calibration Procedure.

Substituting Eq. 15b into Eq. 8 provides Eqs. 16a and 16b, and 17a and 17b for Fourier Coefficients, (note that the DC term is unchanged):

$$m\alpha_2 = \alpha_2 \cos 2C_s - \beta_2 \sin 2C_s \tag{16a}$$

$$m\beta_2 = \alpha_2 \sin 2C_s + \beta_2 \cos 2C_s \tag{16b}$$

$$m\alpha_4 = \alpha_4 \cos 4C_s - \beta_4 \sin 4C_s \tag{17a}$$

$$m\beta_4 = \alpha_4 \sin 4C_s + \beta_4 \cos 4C_s \tag{17b}$$

Continuing, the present invention simultaneously measures the Intensity of a multiplicity of essentially single wavelengths with a Photo Array, to determine Fourier Coefficients. And as the Diode Elements in the Photo Array are operated in a Charge Integration Mode, it is necessary to utilize a Hadamard analysis of the signal. In the preferred embodiment of the present invention, the Diode Array is synchronously read-out exactly sixteen (16) times during each rotation of the Rotating Compensator. The time varying signal, which results from modulation imposed by the Rotating Compensator, is given by Eq. 18. Eq. 19 represents a measured value at a given channel in a Photo Array for the i'th scan measured during the rotation.

$$s(t)=I_o \cdot (DC + \alpha_2 \cos 2t + \beta_2 \sin 2t + \alpha_4 \cos 4t + \beta_4 \sin 4t) \tag{18}$$

$$h_i = \int_{(i-1) \cdot \frac{\pi}{8}}^{i \cdot \frac{\pi}{8}} s(t) dt \tag{19}$$

Substituting Eq. 18 into Eq. 19 and rearranging terms provides the following expressions, (Eqs. 20–24), for the Fourier Coefficients:

$$DC = \frac{h_1 + h_2 + h_3 + h_4 + h_5 + h_6 + h_7 + h_8 + h_9 + h_{10} + h_{11} + h_{12} + h_{13} + h_{14} + h_{15} + h_{16}}{4 \cdot \pi \cdot I_0} \tag{20}$$

$$\alpha_2 = \frac{h_1 + h_2 - h_3 - h_4 - h_5 - h_6 + h_7 + h_8 + h_9 + h_{10} - h_{11} - h_{12} - h_{13} - h_{14} + h_{15} + h_{16}}{8 \cdot I_0} \tag{21}$$

$$\beta_2 = \frac{h_1 + h_2 + h_3 + h_4 - h_5 - h_6 - h_7 - h_8 + h_9 + h_{10} + h_{11} + h_{12} - h_{13} - h_{14} - h_{15} - h_{16}}{8 \cdot I_0} \tag{22}$$

$$\alpha_4 = \frac{h_1 - h_2 - h_3 + h_4 + h_5 - h_6 - h_7 + h_8 + h_9 - h_{10} - h_{11} + h_{12} + h_{13} - h_{14} - h_{15} + h_{16}}{8 \cdot I_0} \tag{23}$$

$$\beta_4 = \frac{h_1 + h_2 - h_3 - h_4 + h_5 + h_6 - h_7 - h_8 + h_9 + h_{10} - h_{11} - h_{12} + h_{13} + h_{14} - h_{15} - h_{16}}{8 \cdot I_0} \tag{24}$$

Equations 20–24 provide the means for extracting the Fourier Coefficients for the Rotating Compensator signal from the (hi) values which are measured by the Photo Array Diode Elements during continuous rotation of the Rotating Compensator.

It is emphasized that good quality electronics which employ the Video Integration Read-Out technique have been found to be very conducive to accurately measuring Fourier Coefficients using Photo Array Diode Elements. It is to be understood that said good quality electronics interface output signals from Photo Array Diode Elements to a computer system which collects and analyzes data. Preferred "Off-The-Shelf-Systems" which include good quality electronics, suitable for use in the present invention Rotating Compensator Material System Investigation System, are Zeiss Diode Array Spectrometer systems identified by manufacturer numbers selected from the group: MMS1 (300–1150 nm); UV/VIS MMS (190–230 nm); UV MMS (190–400 nm); AND IR MMS (900–2400 nm). Said Zeiss systems also include Dispersive Optics and Diode Element containing Photo Arrays. The Zeiss systems include twelve (12) bit dynamic range readout electronics, which provides a voltage pulse output. The present invention system provides additional good-quality electronics in the form of an integrator and Analog to Digital Converter. In use, the scanning rate of Diode Elements in a Zeiss system Photo Array is synchronized with the rotation of the Rotating Compensator of the present invention Rotating Compensator Material System Investigation System. Said synchronization is accomplished utilizing standard digital logic, and Diode Elements in the Photo Array are scanned sixteen (16) times during each rotation of the Rotating Compensator. It is further noted that the present invention preferably effects rotation of the Rotating Compensator with a hollow shaft Stepper Motor. A sequence of reference pulses is generated by a sensor attached to the Rotating Compensator, with said reference pulses being provided to good quality electronics simultaneous with the data provided by the Photo Array Diode Elements. Said reference pulses allow correlation of the angular position of the Rotating Compensator with data provided by the Photo Array Diode Elements.

Regarding Photo Array data, it is further noted that authors An and Collins describe some of the non-idealities which can be present when using a Photo Array Detector in a Spectroscopic Rotating Compensator Material System Investigation System. With the exception of the An and Collins correction for "Stray Light" (see An and Collins Eq. 13), however, none of the Photo Array non-ideality corrections which were presented in their paper were found necessary in implementing the preferred embodiment of the present invention. However, to allow a non-ideal Photo Array to be used in the present invention, the relevant corrections for a Image Persistence, and for Read Time in a Spectroscopic Rotating Compensator Material System Investigation System in which sixteen (16) Diode Element Scans are acquired for each Rotating Compensator revolution were derived, and are provided in Eqs. 25–34.

Image Persistence correction, where 'x' is the magnitude of the non-ideality:

$$ip\alpha_2 = \alpha_2 - 0.5 \cdot x \cdot [(2-\sqrt{2}) \cdot \alpha_2 + \sqrt{2} \cdot \beta_2] \quad (25)$$

$$ip\beta_2 = \beta_2 - 0.5 \cdot x \cdot [(2-\sqrt{2}) \cdot \beta_2 + \sqrt{2} \cdot \alpha_2] \quad (26)$$

$$ip\alpha_4 = \alpha_4 - x \cdot (\alpha_4 + \beta_4) \quad (27)$$

$$ip\beta_4 = \beta_4 - x \cdot (\beta_4 - \alpha_4) \quad (28)$$

$$ipDC = DC \quad (29)$$

Read Time correction, where 'p' is the channel read time of the diode array:

$$c\alpha_2 = ip\alpha_2 - 0.5 \cdot \rho \cdot [(1+\sqrt{2}) \cdot ip\alpha_2 + ip\beta_2] \quad (30)$$

$$c\beta_2 = ip\beta_2 - 0.5 \cdot \rho \cdot [(1+\sqrt{2}) \cdot ip\beta_2 - ip\alpha_2] \quad (31)$$

$$c\alpha_4 = ip\alpha_4 - \rho \cdot (ip\alpha_4 + ip\beta_4) \quad (32)$$

$$c\beta_4 = ip\beta_4 + \rho \cdot (ip\alpha_4 - ip\beta_4) \quad (33)$$

$$cDC = \left(1 - \frac{4 \cdot \rho}{\pi}\right) \cdot ipDC \quad (34)$$

Eqs. 25–34 can be applied after Eqs. 10–17 to account for non-idealities in the Photo Array Diode Element readout. The Image Persistence and Read-Out non-ideality factors 'X' and 'p' can also be determined by defining them as Fit Parameters in a Calibration Regression procedure presented in the following section of this Specification.

For demonstration purposes, considering now the present invention Spectroscopic Rotating Compensator Material System Investigation System to be a Rotating Compensator Ellipsometer System with Diode Element Array read-out, it must be understood that to acquire usable data, Calibration must be performed. Said calibration provides numerical values for Azimuthal Orientation Off-set Angles of Polarizer, Analyzer and Compensator with respect to a Material System Frame of Reference, along with the Retardance of the Rotating Compensator as a function of Wavelength. In addition, Calibration Parameters to compensate non-idealities in Diode Elements in a Photo Array are calibrated.

The foundation of the Calibration Procedure was first announced in the 1993 paper by Johs, published in Thin Film Solids, cited in the Background Section herein. The same basic Calibration Procedure technique is further developed in Co-pending Patent application Ser. No. 08/618,820 which describes calibration of a Rotating Compensator Ellipsometer System utilized in the Infra-red (IR) band of wavelengths. Both identified references, however, describe typical application of the Regression based Calibration technique to one (1) wavelength at a time. While this method does work, it can require two-hundred-fifty-six (256) sets of Calibration Parameters where a two-hundred-fifty-six (256) Diode Element Photo Array is utilized, with each Diode Element serving to monitor an essentially single wavelength. (Note, as the electromagnetic spectrum is continuous, an essentially single wavelength is to be understood to be a small range of wavelengths centered around some wavelength, which essentially single wavelength is intercepted by a Diode Element in a Photo Array).

In practice of the present invention a "Global" regression procedure is typically performed on a Two (2) Dimensional Data Set. Typically Polarizer Azimuthal Angle and Wavelength are selected as Data Set Independent variables, although electromagnetic beam Angle-of-Incidence with respect to a Material System surface could be selected as an Independent variable instead of, for instance, Wavelength or Polarizer Azimuthal Angle. It is also noted that the Regression based Calibration described in Co-pending application Ser. No. 08/618,820 required that two (2), at least two (2) Dimensional Data Sets be provided in each Regression procedure. The two Data Sets are obtained with different investigated Material System configurations being employed. For instance, Data Sets utilizing two different Material Systems, or one Material System present and a "Straight-through" configuration might be utilized. (Note, a "Straight-through" configuration results when no 22 Material System is present, and an electromagnetic beam is caused to pass sequentially through a Polarizer, Compensator and Analyzer then enter a Photo Array Detector System, without interacting with a Material System). The present invention, in contrast, requires that only one Data Set be present. Said Data Set can be obtained with the Ellipsometer in Material System present or Straight-through configuration, although some benefits are realized when a Material System is utilized, (discussed supra herein). Of course, the present invention can be practiced utilizing two Data Sets.

As mentioned, the Regression based Calibration procedure of the present invention requires that an at least Two (2) Dimensional Data Set be experimentally obtained. Typically said Two (2) Dimensional Data Set has as Independent Variables, Polarizer, (where the Rotating Compensator is placed after a Material System), Azimuthal Angle, and Wavelength. Where a Rotating Compensator is placed before a Material System, an Analyzer Azimuthal Angle is utilized. As mentioned, Angle-of-Incidence of an investigation Electromagnetic Beam with respect to an investigated Material System surface can be substituted for an Analyzer or Polarizer Azimuthal Angle settings, but this is not preferred as Material System PSI and DELTA values vary therewith. Also, it is generally simpler to vary a Polarizer or Analyzer Azimuthal Angle in most Ellipsometer systems in practice. Continuing, data is simultaneously obtained from many Diode Elements, (which correspond to different Wavelengths), and subjected to the Hadamard analysis inherent in Eqs. 20–24, infra to provide Fourier Coefficients present in Eq. 18. (It is noted that a Photo Array can contain 256, 1024 or 2048 Diode Elements, and some thereof might provide a signal which of too small an intensity to be utilized. The present invention allows for utilizing only a user selected group of signals for this and other reasons).

It will be noted that Eqs. 8 and 18 contain a D.C. term "$I_o$". This can be selected as a Fit Parameter in a Regression Procedure or a Normalization procedure can be implemented. Said Normalization can be with respect to the D.C. term, or a Normalizing Parameter can be included. The following Eqs 35a, 35b and 35c provide possible Normalizing Parameters:

$$Norm = DC \quad (35a)$$

$$Norm = \sqrt{(\alpha_2)^2 + (\beta_2)^2 + (\alpha_4)^2 + (\beta_4)^2 + (DC)^2} \quad (35b)$$

$$Norm = \sqrt{(\alpha_2)^2 + (\beta_2)^2 + (\alpha_4)^2 + (\beta_4)^2} \quad (35c)$$

Eq. 35a provides for Normalizing with respect to the D.C. term, Eq. 35b provides for Normalizing to a Parameter which depends on the D.C. Term and the Fourier Coefficients, while Eq. 35c provides for Normalizing to a Parameter which depends on Fourier Coefficients but not the D.C. Term. If Fourier Coefficients are not Normalized, (ie. the D.C. Term "$I_o$" is not included as a Fit Parameter in a Calibration Parameter evaluating Regression Procedure, or Normalization is not performed), it should be appreciated that a "Floating" value result will be obtained for Calibration Parameters provided by application of the Calibration Parameter evaluating Regression onto said Fourier Series Coefficient values. As mentioned infra herein, the D.C. Component "$I_o$" can be difficult to evaluate, often requiring a "Shutter" to block background light, dark current, readout electronics voltage offsets etc. As well, the D.C. component is more susceptible to instrumentation drift. As a result, use of Eq. 35c is preferred in the present invention Calibration Procedure to use of Eqs. 35a and 35b and to including "$I_o$" in a Regression Procedure for evaluating Calibration Parameters. (Note that calibration data is taken with the Rotating Compensator Sample System Investigating System in a "Sample Present", rather than a "Straight Through" configuration, where such Eq. 35c normalization is practiced).

Normalized Fourier Coefficients can be then represented by Eqs 36–39:

$$n\alpha_2 = \frac{\alpha_2}{Norm} \tag{36}$$

$$n\beta_2 = \frac{\beta_2}{Norm} \tag{37}$$

$$n\alpha_4 = \frac{\alpha_4}{Norm} \tag{38}$$

$$n\beta_4 = \frac{\beta_4}{Norm} \tag{39}$$

A Global Calibration Data Set can be represented by Eq. 40:

$$MFD_{P,n} = \{(n\alpha_2)_{P,n}, (n\beta_2)_{P,n}, (n\alpha_4)_{P,n}, (n\beta_4)_{P,n}\} \tag{40}$$

where MFD stands for Measured Fourier Data, and where "P" is the Polarizer Angle and constitutes one Independent Variable, (and is typically varied within the range of from zero (0.0) to one-hundred-eighty (180) degrees, in ten (10) degree steps), and where "n" identifies the index of a selected Diode element, (channel), in the Photo Array, or alternatively stated, identifies a Second Independent Variable, (ie. Wavelength). It is noted that a typical system configuration would make use of Diode Elements (channels) 30–250 in a 256 channel Photo Array. The term "Global" emphasizes the presence of Wavelength Dependence. Utilizing the just described "P" range settings and Wavelength range, Eq. 41 indicates that the Global MFD Data Set would contain:

(180/10 + 1 polarizer settings) × (250 − 30 + 1 channels) × (4 Fourier components) = 16,796 values (41)

It is further noted that an approximate error in Fourier Data ( denoted $\sigma MFD_{P,n}$), can be estimated from signal to noise at each Detector Channel, and subsequently used in the Regression Analysis of the Experimentally Obtained Data Set.

Continuing, use of Eqs. 3–17, 35–39 and (25–34 if Photo Array nonidealities are included), allows one to calculate, (ie. mathematically predict), values of Normalized Fourier Coefficients as in Eqs 36–39, which will be experimentally measured by a present invention Rotating Compensator Material System Investigation System. However, to make said mathematical prediction requires that Material System PSI and DELTA values be known, the Offset Angles $P_s$, $A_s$, and $C_s$ be known, and that Compensator Retardation "$\delta$" be known as well as any other Compensator non-idealities, and that the Photo Array nonidealities "x" and "$\rho$" be known if necessary. Mathematically this can be represented by Eq. 42:

$$PFD_{P,n}(P,\psi_n, \Delta_n, (P_s)_n, (C_s)_n, (A_s)_n, \delta_n, x_n, \rho_n) \tag{42}$$

Eq. 42 states that a Predicted Fourier Data (PFD) Set at a given Polarizer Azimuth and Photo Array Channel (Wavelength), is a function of identified variables, which variables constitute Calibration Parameters which must be provided numerical values. The present invention Regression procedure provides means for numerically evaluating the Calibration Parameters.

In all known prior art, separate Regression procedures have been carried out at each utilized Wavelength. If Two-Hundred (200) Wavelengths were utilized, then Two-Hundred (200) separate values for $P_s$, $A_s$, $C_s$ etc. would be obtained. The present invention Regression Procedure, however, teaches that Calibration Parameters as a function of an Independent Variable, (eg. Wavelength), can be "Parameterized". That is, a mathematical relationship requiring only a few (eg. perhaps two (2) or three (3) Parameters), can be generated to describe a functional relationship between the Calibration Parameter and the Independent Variable (eg. Wavelength), and the present invention Regression Procedure utilized to evaluate said Two (2) or Three (3) Parameters. For example, the Polarizer Azimuthal Offset ($P_s$) might be constant for all Wavelengths. Should this be the case then said Polarizer Azimuthal Offset ($P_s$) can be evaluated and stored, rather than, for instance, Two-Hundred (200) separate values at Two-Hundred (200) separate Wavelengths. In this instance, Eq. 43 indicates that a Global Calibration Parameter can be defined:

$$(P_s)_n = gP_s \tag{43}$$

In general, any of the discretely defined Calibration Parameters identified in Eq. 42, could be replaced by a Global Parametric Function as defined in Eq. 44:

$$CP_n = gCP(n, p_1, p_2, \ldots, p_k) \tag{44}$$

where $CP_n$ stands for any Calibration Parameter which is discretely defined for each "n"'th channel, (ie. the "n"'th Wavelength), and "gCP" is a global Parametric Function (as a function of an "n"'th channel number and "k" Calibration Parameters "p1 . . . pk" which replace $CP_n$. A Parametric Function can be of any mathematical form, such as, but not limited to, polynomial, rational or trancendental (in the case of $\psi_n$ and $\Delta_n$, a Parametric Function could be calculated from a multi-layer optical model for a Material System, using known Material Optical Constants and Parameterized Film Thicknesses). The important characteristic of a Parametric Function being that:

1. It accurately represents the behavior of the Calibration Parameter at each Independent Variable (eg. Photo Array Channel or Wavelength).
2. It accurately represents the behavior of the Calibration Parameter utilizing fewer Parameters than would be required to simply evaluate Calibration Parameters at each utilized Independent Variable (eg. Wavelength).

In terms of Eq. 44 this can be stated that "k" (the number of Calibration Parameters), is less than "n" (the number of channels).

It is to be understood that preferred Global Parameter Function form utilized in the present invention depends upon the particular embodiment utilized, (eg. the Compensator type utilized). It is also within the scope of the present invention Regression based Calibration Parameter evaluation Procedure to represent some Calibration Parameters with Global Parametric Functions, and to represent other Calibration Parameters discretely. Three examples of Global Parametric Function utilizing Models follow directly.

Global Regression Mode (GRM) 1.

This (GRM) requires that five (5) Calibration Parameters be evaluated. Eqs. 45–47 provide equations for Predicted Fourier Data (PFD):

$$PFD_{P,n}(P, \psi_n, \Delta_n, gP_s, gC_s, gA_s, g\delta(n, p_0, p_1)) \tag{45}$$

$$\text{where } g\delta(n, p_0, p_1) = [p_0 \cdot 90 \cdot (1 + p_1/[w(n)]^2)]/w(n) \tag{46}$$

$$\text{and } w(n) = C_0 + C_1 \cdot n + C_2 \cdot n^2 \tag{47}$$

where w(n) returns a wavelength of electromagnetic radiation (in nanometers), corresponding to the "n"'th channel of a Photo Array, where $C_0$, $C_1$ and $C_2$ are wavelength Calibration Parameters. In the case where a previously identified Ziess Diode Array Spectrometer Systems is utilized, said $C_0$, $C_1$ and $C_2$ Calibration Parameters are provided by the manufacturer, and Eq. 47 can be utilized to provide Wavelength given a Photo Array Channel number. The Global Retardance provided by a Compensator as a function of Wavelength is given by Eq. 46. Eq. 46 provides an Inverse Wavelength relationship, where "$p_0$" is a Wavelength, (in nanometers), at which said Compensator is a "Quarter-Wave-Plate" and demonstrates a Ninety (90) degree Retardation, and "$p_1$" accounts for the Dispersive effects in the Optical Properties of the Compensator. Higher order terms can be added to Eq. 46.

In this (GRM) Mode 1, the Azimuthal Offset Calibration Parameters are considered constant for all Wavelengths. Therefore, using (GRM) Mode 1, only Five (5) Global Calibration Parameters:

$$(gP_s, gC_s, gA_s, p_0, p_1)$$

in addition to Material System PSI and DELTA:

$$\psi_n \text{ and } \Delta_n$$

need be evaluated by a present invention Regression Procedure.

GLOBAL REGRESSION MODE (GRM) 2.

This Mode is similar to (GRM) 1, but the $P_s$ Calibration Parameter is defined as a Global Calibration Parameter, (ie. it is a constant independent of Photo Array Channel Number "n"). Again, the Retardance of the Compensator is Parameterized by Eqs. 46 and 47. Values for $C_s$ and $A_s$ are allowed to take on discrete vales at each Photo Array Channel, however, Eq. 48 indicates the relationship:

$$PFD_{P,n}(P, \psi_n, \Delta_n, gP_s, (C_s)n, (A_s)_n, g\delta(n, p_0, p_1)) \tag{48}$$

GLOBAL REGRESSION MODE (GRM) 3.

In this (GRM) 3 Mode, only $P_s$ is defined as a Global Parameter, and all other system Calibration Parameters are allowed to take on discrete values at each Photo Array Channel. Eq. 49 indicates this relationship:

$$PFD_{P,n}(P, \psi_n, \Delta_n, gP_s, (C_s)_n, (A_s)_n, \delta_n) \tag{49}$$

REGRESSION

The present invention Regression Analysis which evaluates the Calibration Parameters identified infra herein utilizes standard non-linear regression analysis. First a $\chi_2$ metric is defined by Eq. 50 to quantify Error between Calculated Predicted Fourier Data (PFD) and Experimentally Measured Fourier Data (MFD).

$$\chi^2 = \sum_P \sum_n \left( \frac{MFD_{P,n} - PFD(P, n, p_k)}{\sigma MFD_{P,n}} \right)^2 \tag{50}$$

Eq. 50 is a simplified way of stating that overall error between measured and predicted Calibration Data Sets is given by the squared difference between each measured and corresponding calculated predicted Fourier data, normalized by the approximate error at each measured data point ($\sigma MFD_{P,n}$), and summed over all the Polarizer and Wavelength (Channel) setting values. Eq. 51 provides a more riggerous mathematical definition.

$$\chi^2 = \sum_P \sum_n \left[ \left[ \frac{(m\alpha_2)_{P,n} - p\alpha_{2(P,n,p_k)}}{(\sigma\alpha_2)_{P,n}} \right]^2 + \left[ \frac{(m\beta_2)_{P,n} - p\beta_{2(P,n,p_k)}}{(\sigma\beta_2)_{P,n}} \right]^2 \ldots + \left[ \frac{(m\alpha_4)_{P,n} - p\alpha_{4(P,n,p_k)}}{(\sigma\alpha_4)_{P,n}} \right]^2 + \left[ \frac{(m\beta_4)_{P,n} - p\beta_{4(P,n,p_k)}}{(\sigma\beta_2)_{P,n}} \right]^2 \right] \tag{51}$$

In Eqs. 50 and 51, $p_k$ represents the "k" adjustable system Calibration Parameters required to calculate (PFD). The well known Marquardt-Levenberg non-linear Algorithm, as described in the Johs paper cited in the Background Section herein, can be used to itteratively adjust system Calibration Parameters $p_k$ to minimize error.

It is noted that good initial values are required to practice Regression which converges rapidly. The present invention obtains good starting values for use in the Global Regressions described, by performing a number of non-global Regressions at a multiplicity of discrete Wavelengths. The resulting ranges of values for the various Calibration Parameters then allows educated selection for Global Regression starting values.

It is also noted that Global Regression can be performed utilizing only data from every "N"'th Channel, (eg. every "N"3"'th Wavelength), to reduce required Regression procedure time to arrive at convergence. This approach to Regression is still to be considered as Global.

Once the present invention Spectroscopic Rotating Compensator Material System Investigation System is calibrated, it is possible to take data from unknown samples therewith and obtain PSI and DELTA plots therefore. Kleim et al., describes equations for PSI ($\psi$) and DELTA ($\Delta$) and these equations are provided as Eq. 52 and 53 herein:

$$\tan(2 \cdot \Psi) = \frac{\sqrt{[(\alpha_2)^2 + (\beta_2)^2] \cdot \left( \frac{1 - \cos(\delta)}{\sin(\delta)} \right)^2 + 4 \cdot (\beta_4 \cdot \cos(2 \cdot P) - \alpha_4 \cdot \sin(2 \cdot P))^2}}{2 \cdot (\alpha_4 \cdot \cos(2 \cdot P) + \beta_4 \cdot \sin(2 \cdot P))} \tag{52}$$

$$\tan(\Delta) = \left( \frac{1 - \cos(\delta)}{2 \cdot \sin(\delta)} \right) \cdot \frac{\alpha_2 \cdot \sin(2 \cdot P) - \beta_2 \cdot \cos(2 \cdot P)}{\alpha_4 \cdot \sin(2 \cdot P) - \beta_4 \cdot \cos(2 \cdot P)} \tag{53}$$

In these equations the Analyzer should be set to ±45 degrees. Also, prior to applying Eqs. 52 and 53 the measured Fourier Data should be transformed into "ideal" Fourier Data by application of Eqs. 15a, 15b, 16a, 16b, 17a and 17b as well as Eqs. 25–34. Kleim et al. also describes the advantages of performing a zone-averaged measurement in a Rotating Compensator System, (ie. averaging the PSI and DELTA extracted from measurements with the Analyzer A set to first, +45 Degrees, and second to −45 Degrees. This can be concurrently practiced with the present invention to further improve the accuracy of data measurement.

It is also noted that an alternative approach to obtaining Material System PSI and DELTA characterizing data, is to perform a Calibration Procedure on a present invention Spectroscopic Rotating Compensator Material System Investigation System in a Sample Present Mode, with said Material System present therein.

The present invention will be better understood by reference to the Detailed Description Section of this Disclosure, in conjunction with the accompanying Drawings.

SUMMARY OF THE INVENTION

It is therefore a primary purpose of the present invention to teach a Spectroscopic Rotating Compensator Material System Investigation System, including at least one Photo Array comprised of a multiplicity of Diode Elements, for simultaneously detecting a Multiplicity of Wavelengths, which Spectroscopic Rotating Compensator Material System Investigation System can utilize both Achromatic and non-Achromatic Compensators of Berek-type with Optical Axis perpendicular to a surface thereof, and/or with Compensators with Optical Axis parallel to a surface thereof; and which Spectroscopic Rotating Compensator Material System Investigation System can be realized utilizing off-the-shelf Compensator and Spectrometer System components.

It is another primary purpose of the present invention to teach, in the context of a Spectroscopic Rotating Compensator Material System Investigation System, Evaluation of Calibration Parameters in a Mathematical Model thereof by a Mathematical Regression based technique involving utilization of, typically, a single at least Two Dimensional Data Set, obtained with the Spectroscopic Rotating Compensator Material System Investigation System oriented in a "Material System present" or in a Straight-through" configuration.

It is yet another purpose of the present invention to teach that, where beneficial and desirable, Parameterization of Calibration Parameters, (such as Azimuthal Orientation Angle of Polarizer, Compensator(s) and Analyzer, and Material System PSI and DELTA, and Compensator Representing Matrix Components), as a function of a Data Set variable, (such as Wavelength, or Polarizer and/or Analyzer Azimuthal Angle Rotation, or Angle-of-Incidence of an electromagnetic beam with respect to a surface of a Material System being investigated), to reduce the number of Calibration Parameters which need be evaluated during a mathematical regression based Calibration Procedure, should be precticed.

It is a purpose of the present Disclosure to provide experimentally determined documentation of the utility of the present invention Spectroscopic Rotating Compensator Material System Investigation System, in the form of results obtained from practice of the Mathematical Regression Calibration Method, and the Material System Investigation Data Acquisition Method.

BRIEF DESCRIPTION OF THE DRAWINGS

FIG. 9a shows a Fiber Optic which is essentially circular at the left side and which becomes of a "slit" shape at the right side.

FIG. 9b shows a Fiber Optic which is essentially circular shaped along the entire length thereof, and which provides input to a "Slit" per se.

FIG. 9c shows a Trifrucated Fiber Optic which is essentially circular at the left side, which trifrucates and then is exemplified as becoming circular or of a "slit" shape at the right side.

FIG. 9d shows a Berek-type Compensator with an Optical Axis perpendicular to a surface thereof.

FIG. 9e shows a Compensator with an Optical Axis parallel to a surface thereof.

FIG. 9f demonstrates construction of a Zero-Order Quartz Waveplate from two Multiple Order waveplates.

DETAILED DESCRIPTION
PRESENT INVENTION SYSTEM

Figure 1:
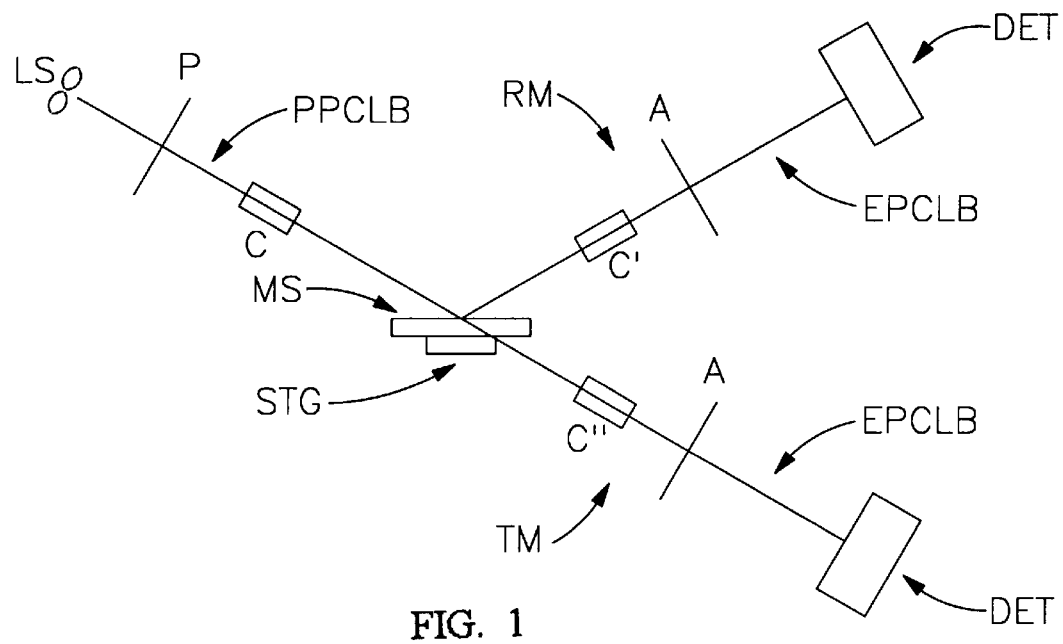
FIG. 1 shows the basic components of Reflectance and Transmission Mode Material System Investigation Systems which can be operated in Spectroscopic Rotating Compensator Material System Investigation System (eg. Ellipsometer System), Modes.

Referring now to FIG. 1, there is demonstrated a Material System Investigation System, (eg. an Ellipsometer System), with provision to investigate a Material System (MS) in either a Reflection Mode (RM) or a Transmission Mode (TM). It is to be noted that said Material System investigation System is generally comprised of a Source of a Polychromatic Beam of Electromagnetic Radiation (LS), a Polarizer (P), a Material System supporting Stage (STG), an Analyzer (A) and a Detector Elements (DE's) containing Photo Array Detector System (DET). Also note, however, that FIG. 1 shows Reflection Mode System Compensator(s) (C) and (C') and Transmission Mode System Compensators (C) and (C") as present. It is to be understood that a Compensator can be placed ahead of, and/or after a Material System (MS) supporting Stage (STG) in either a Reflection Mode or Transmission Mode System. That is only Compensator (C) or (C') or both Compensators (C) and (C') can be present in a Reflection Mode System (RM), and only Compensator (C) or (C') or both Compensators (C) and (C") can be simultaneously present in the Transmission Mode System (TM).

Now, the configuration in FIG. 1 could be operated as a Rotating Polarizer or Rotating Analyzer System. The present Invention Rotating Compensator Material System Investigation System, however, in the preferred operational mode, essentially fixes the Polarizer (P) and Analyzer (A) during Data Acquisition from a Material System (MS) which is placed upon the Material System supporting Stage (STG), and causes at least one present Compensator ((C), and/or (C') or (C) and/or (C")), to Rotate during said Data Acquisition. This serves to effectively enter a continuously varying retardance between Orthogonal Components in a Polarization Beam of Electromagnetic Radiation exiting said Compensator which is caused to rotate. Where two (2) Compensators are present, one before (C) and one after ((C') or (C")) a Material System placed upon said Material System (MS) supporting Stage (STG), only one, or both said Compensator (s) can be caused to Rotate in use. If both Compensators are caused to rotate, both can be rotated a the same rotation speed, or different rotation speeds can be utilized. It is further noted that fixing the Polarizer (P) and Analyzer (A) in use provides another benefit in that polarization state sensitivity to input and output optics during data acquisition is essentially non-existent. This allows use of Optic Fibers, Mirrors, Lenses etc. for input/output.

It is also mentioned that in the following it will be generally assumed that a Material System (MS) under investigation by a present invention Spectroscopic Rotating Compensator Material System Investigation System is positioned upon the Material System Supporting Stage (STG). This need not be the case, as is described in co-Pending Application Serial No. 08/727,700. For instance, a Material System (MS) can be positioned in a Magneto-Optic System which is physically too large to be supported by said Material System Supporting Stage (STG). In such a case, an Electromagnetic Beam Directing Means (eg. a Mooney Rhomb or a Mirror etc), can be placed upon said Material System Supporting Stage (STG) and without realigning a present invention Source of Polychromatic Electromagnetic Beam (LS) and said Detector Element (DE) containing Photo Array Detector System (DET), a Polychromatic Electromagnetic Beam provided by said Source of Polychromatic Electromagnetic Beam (LS) can be caused to interact with said remotely positioned Material System (MS), and with said Electromagnetic Beam Directing Means, thereby being directed into said Detector Element (DE) containing Photo array Detector System (DET).

Figure 2:
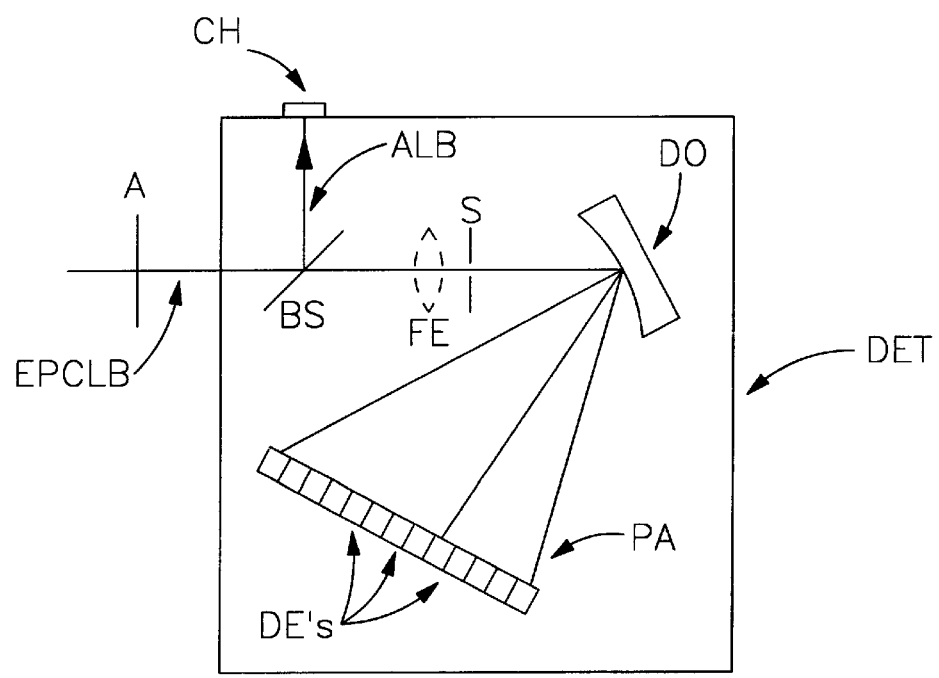
FIG. 2 shows a Spectrographic Diode Array Spectrometer System Detector.

Continuing, the present invention utilizes a Polychromatic Source of Electromagnetic Radiation (LS), and FIG. 2 shows that the Detector Elements (DE's) containing Photo Array Detector System (DET) in the present invention is, in the preferred embodiment, comprised of a Photo Array which consists of a number of Diode Elements (DE's). In use a Dispersive Optics (DO) receives a Polychromatic Electromagnetic Beam (EPCLB) which has interacted with a Material System (MS) and passed through said Analyzer (A), and diffracts said Polychromatic Electromagnetic Beam (EPCLB), such that each Photo Array (PA) Diode Element (DE) intercepts an Essentially Single Wavelength, (eg. a small band of wavelengths centered about a central single wavelength). Note that a Focusing Element (FE) is shown in a dashed line format to indicate that its presence is optional. The Focusing Element (FE), when present, serves to provide a focused Polychromatic Beam of Electromagnetic Waves at the input to said Detector Elements (DE's) containing Photo Array etector System (DET), and the Detector System (DET) provides signals developed by the Diode Elements (DE's) in a sequential output or a parallel output from the Diode Elements (DE's). It is emphasized that a preferred Detector Elements (DE's) containing Photo Array Detector System (DET) is an "Off-the-Shelf-System" which includes a Focusing Element (FE), and provides a self contained Dispersive Optics (DO) and Diode Element (DE) Array. The "Off-The-Shelf-System" of said preferred embodiment of the present Rotating Compensator Material System Investigation System is a Zeiss Diode Array Spectrometer System identified by manufacturer numbers in the group: (MMS1 (300–1150 nm); UV/VIS MMS (190–230 nm); UV MMS (190–400 nm); AND IR MMS (900–2400 nm)). Said identified Zeiss systems provide a very compact system comprising a multiplicity of Detector Elements (DE's), and provide focusing via a Focusing Element (FE), Slit (S), and single concave holographic grating dispersive optics (DO), as generally represented by FIG. 2.

Note that FIG. 2 also shows the presence of a Beam Splitter (BS) and a Cross Hair containing Reticule CH) in the Detector Elements (DE's) containing Photo Array Detector System (DET). If the Beam Splitter (BS), the Dispersive Optics (DO), the Focusing Element (FE), the Detector Elements (DE's) containing Photo Array (PA), and the Cross Hair containing Reticule (CH) are mounted so as to move as a rigid unit, then it should be appreciated that causing an Alignment Electromagnetic Radiation Beam (ALB) which reflects to said Cross Hair containing Reticule(CH) to be present near a Cross Hair crossing point can effect good alignment of the Detector Elements (DE's) containing Photo Array Detector System (DET) with respect to an entering Polarized Beam of Electromagnetic Radiation (EPCLB). In practice such an arrangement has been found to work very well. It is further noted that the element identified as (CH) could represent a Quadrature Photodetector and Automatic Alignment Means, or other functionally suitable system.

It is also noted that a present invention Compensator (C) (C'), (C") is typically an Off-the-Shelf Quarter-Wave-Plate with its Optical Axis in the plane of a surface thereof, (see FIG. 9e), or Berek-type with its Optical Axis perpendicular to a surface thereof, (see FIG. 9d), and is selected without special concern to its Achromatic Operating Characteristics, emphasis added. Note that a Zero-Order Waveplate can be constructed from two (2) Multiple-Order Waveplates of different thicknesses (T1) and (T2) which have Optical Axes oreinted Ninety (90) degrees to one another, such that the overall effect of retardation in in the Zero-Order, (see FIG. 9f). As well, said Compensator (C), (C'), (C") can be made of essentially any functional material such as Quartz or Polymer etc.

Now, and very importantly, even though the Present Invention Rotating Compensator Material System Investigation System is Spectroscopic, (ie. simultaneously operates on a number of Wavelengths in a Beam containing many Electromagnetic Wavelengths, over a range of, for instance, 190–1000 nanometers), a Compensator (C), (C'), (C") utilized therein can provide a Retardance which, for instance, varies inversely with Wavelength and still be usable. A Compensator (C), (C'), (C") does however, typically, have to be of a nature to allow passage of a Polychromatic Electromagnetic Beam therethrough without causing significant Attenuation, Deviation or Displacement in the Direction of Propagation thereof. If this is not the case, difficult to compensate complexities are caused in Detector Elements (DE's) containing Photo Array Detector System (DET) Detector Element Output Signals.

The reason the Present Invention can operate with a Compensator (C), (C'),(C") that does not provide even close to a Constant Ninety (90) Degree Retardance over a range of Wavelengths, (which would constitute Ideal Characteristics), is that a Regression based Calibration Procedure utilized, (see the Disclosure of the Invention Section of this Specification), provides Wavelength dependent Compensation effecting values for Calibration Parameters as required in a developed Mathematical Model of the present invention Rotating Compensator Material System Investigation System. As better described in the Disclosure of the Invention Section of this Disclosure, the Inventors develop a Calibration Parameter Containing Mathematical Model of the present invention Rotating Compensator Material System Investigation System by, for instance, utilizing Matrix Representations for various System Components involved, then multiplies out the Matrices in an appropriate order to provide a Transfer Function. This applies for all Wavelengths monitored by a Detector Elements (DE's) containing Photo Array Detector System (DET) Detector Element (DE). Next, Data Set(s) are Experimentally obtained as a function of wavelength and typically as a function of various settings of the Polarizer (P) or Analyzer (A), (or both could be rotated to various positions), while a Compensator (C) rotates at, typically though not necessarily, Twenty (20) to Thirty (30) Hz. Other rotation speeds can be utilized and if two Compensators are present one or both can be caused to rotate, and if both are caused to rotate, as mentioned infra herein, they can be caused to rotate at the same, or different, speeds. (Note that Data Set(s) could also be achieved utilizing variation of Angle-Of-Incidence of a Beam of Polychromatic Radiation with respect to a Material System under investigation). Calibration Parameters in the Mathematical Model are then evaluated by, typically, Mean-Square-Error based Regression onto the Data Set(s). It is also possible to effectively find Calibration Parameter containing Mathematical Expressions for Coefficients of Mathematical Series, (eg. Fourier Series), which comprise the Mathematical Model Transfer Function, and calculate Numerical Values for the Coefficients from the Data Set(s), then effectively perform Regression of said Calibration Parameter containing Mathematical Expressions for Coefficients of Mathematical Series Transfer Function onto said Numerical Values for the Coefficients from the Data Set(s). It is that a single Two-Dimensional Data Set has been found sufficient to allow excellent Calibration results to be achieved. Said Two-Dimensional Data Set typically is Intensity vs. Wavelength, and Polarizer or Analyzer Azimuthal Rotation Angle settings. In addition, said Two-Dimensional Data Set can be obtained from a present invention Rotating Compensator Material System Investigation System oriented so that a Polychromatic Beam of Electromagnetic Radiation interacts with a Material System (ie. the "Sample Present" Mode—see FIGS. 1, 3, 4, and 5)), or such that said Polychromatic Beam of Electromagnetic Radiation passes through the present invention Rotating Compensator Material System Investigation System without interacting with a Material System, other than a Material System comprised of "Open Atmosphere", (ie. the "Straight-Through" Mode—see FIG. 7). The present invention Rotating Compensator Material System Investigation System can also, of course, be Calibrated utilizing more than one Data Set as well, but as alluded to, this has not been found necessary. This is mentioned as the invention reported in Co-pending Patent application Ser. No. 08/618,820, wherein a Rotating Compensator Material System Investigation System utilized in the Infra-red band of wavelengths, requires that two (2) Data Sets be present, (eg. selected with the Rotating Compensator Material System Investigation System oriented in a manner selected from the group: ("Straight-Through", "Material Sample Present", "Alternative Material Sample Present")). Both Data Sets are simultaneously utilized in a Regression Procedure to evaluate numerous Calibration Coefficients in a Mathematical Model which is described in the Ser. No. 08/618,820 application. The reason that only one (1) Data Set is required to practice the described present invention Calibration Procedure, is that the number of Calibration Parameters required by the Mathematical Model of the present invention, (which is not operated in the Infra-red range of wavelengths), is much fewer than the number of Calibration Parameters required by the Mathematical Model of the Rotating Compensator Material System Investigation System operated in the Infra-red range of wavelengths. The present invention Rotating Compensator Material System Investigation System Mathematical Model typically involves as few as Five (5) Calibration Parameters, (where only one Compensator is present), in combination with simultaneous determination of a Material System PSI and DELTA. (It is noted that a straight-through mode essentially provides open atmosphere as a Material System and that the PSI and DELTA of open atmosphere are forty-five (45) degrees and zero (0.0) degrees, respectively). Said Five (5) Calibration Parameters are Azimuthal Orientation Angles for Polarizer ($P_s$), Analyzer ($A_s$), Compensator ($C_s$), and Compensator Retardance Parameters (P0) and (P1). Equations (45) and (46) serve as further demonstratration of this point. (Note that the ($P_s$), ($C_s$) and ($A_s$) Azimuthal Orientation Calibration Angles can be thought of as serving to align the Polarizer, Compensator and Analyzer Azimuths with a Material System Frame of Reference). Of course, if two Compensators are present then an additional Compensator Orientation Angle (Cs2) and Compensator Retardance Parameters (P0') and (P1') would also have to be evaluated. (It is noted that Retardation entered between orthogonal components of a Polarized Electromagnetic Beam, by a Compensator, is accounted for by a Matrix Component, and typically the r4 term of a Jones Matrix, but such is accounted for by Compensator Retardation Parameters (P0), (P1), (P0'), (P1') in the presently described Calibration Procedure).

Figure 3:
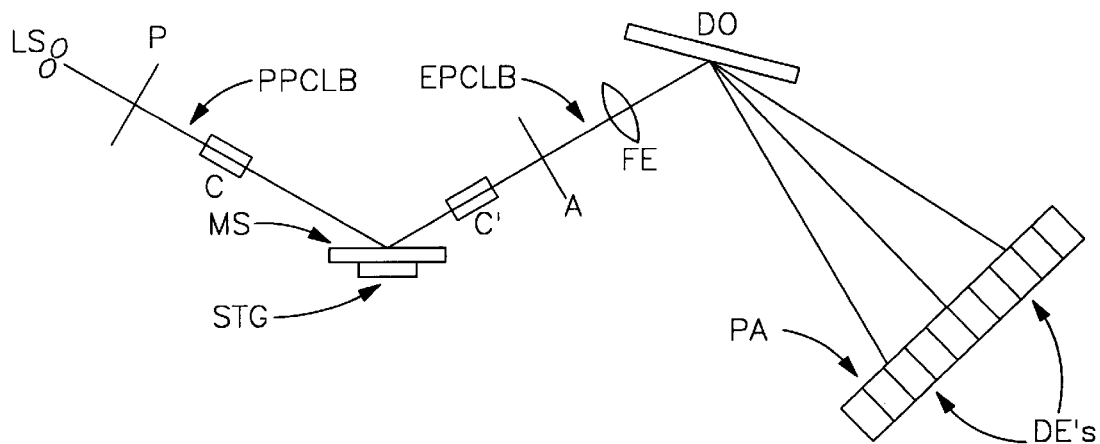
FIG. 3 shows a Reflectance Mode combination of components shown in FIGS. 1 and 2.

Now, it is to be understood that the system of the present invention Spectroscopic Rotating Compensator Material System Investigation System is basically found in a combination of components shown in FIGS. 1 and 2, the basic result of said combination, for a Reflectance Mode System, being shown in FIG. 3. That is, FIG. 3 shows a Spectroscopic Reflectance Mode version of the Rotating Compensator Material System Investigation System shown in FIG. 1, with the FIG. 2 Detector Elements (DE's) containing Photo Array Detector System (DET) shown present directly after the Analyzer (A).

Figure 4:
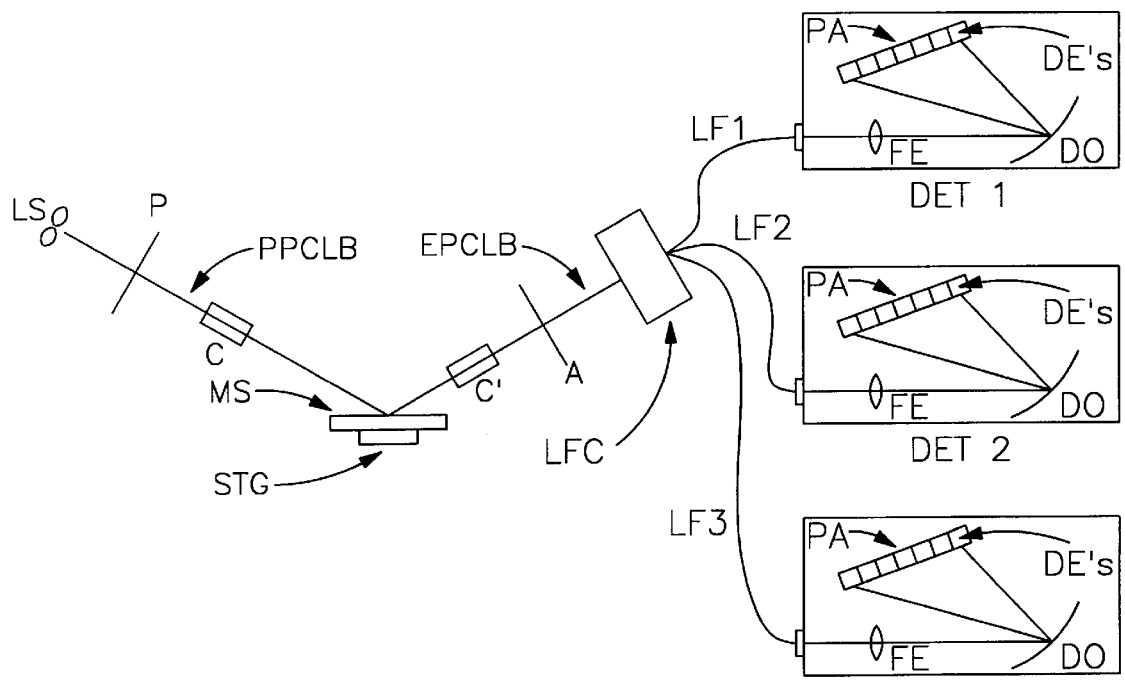
FIG. 4 shows a Reflectance Mode combination of components shown in FIGS. 1 and 2 in which three FIG. 2 Spectrographic Diode Array Spectrometer Systems are present and provided input via light fibers.

FIG. 4 shows another present invention system Reflectance Mode System configuration in which three (3) Detectors (Det 1), (Det 2) and (Det 3) are fed input by Fiber Optics (LF1), (LF2) and (LF3) present in a Fiber Optic Bundle exiting Fiber Optic Connector (LFC). Said Fiber Optic Connector (LFC) receives a Polarized Electromagnetic Beam (EPCLB) exiting the Analyzer (A). (Note that a FIG. 9c at least Bifrucated Fiber Optic could be utilized). Said three (3) Detectors (Det 1), (Det 2) and (Det 3) can be previously disclosed Off-the-shelf Zeiss Diode Array Spectrometers, and can each comprise a Focusing Element (FE) in functional combination with a Dispersive Optics (DO) and a Diode Element (DE) containing Photo Array (PA).

Figure 5:
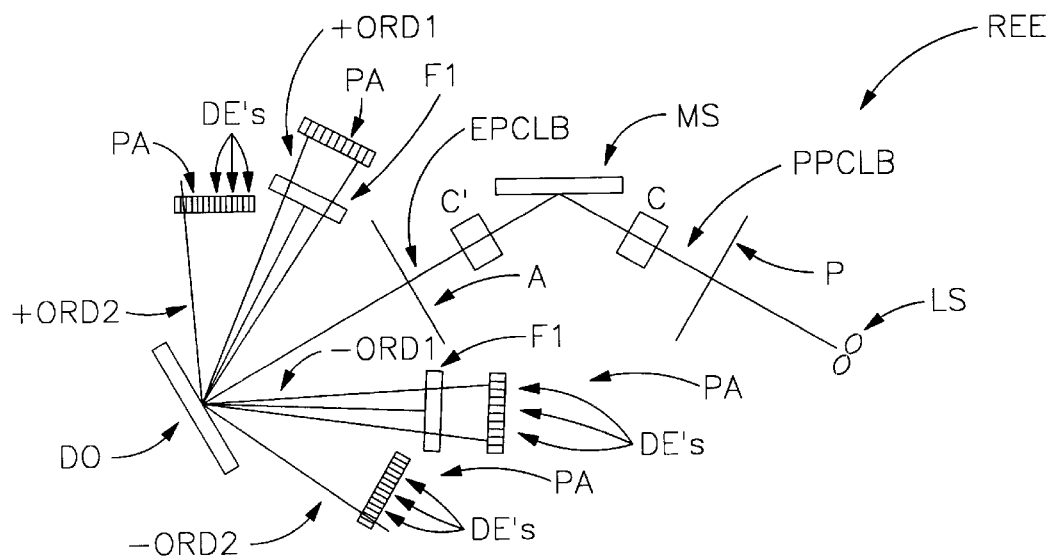
FIG. 5 shows a Reflectance Mode combination of components shown in FIGS. 1 and 2 in which Multiple Orders produced by a Dispersive Optics are intercepted by multiple Photo Arrays.

FIG. 5 shows that the present invention can cause a Polychromatic Beam of Polarized Electromagnetic Radiation (PPCLB) to, after interaction with a Material System (MS), reflect therefrom. FIG. 5 shows that the Reflected Polarized Beam of Electromagnetic Radiation (EPCLB), is caused to impinge upon a Dispersive Optics (DO), (eg. a Diffraction Grating), such that a plurality of Orders (+ORD2, +ORD1, -ORD1 and -ORD2) are produced. Each said Order is comprised of a spectrum of Wavelengths, and FIG. 5 shows that Wavelengths in said Orders (+ORD2, +ORD1, -ORD1 and -ORD2) can be intercepted by Detector elements (DE's) in Photo Arrays (PA). The present invention can, in some embodiments, utilize such a system. It is noted that the Dispersive Optics (DO) is typically rotatable so that the direction each Order of wavelengths generally proceeds from said Dispersive Optics (DO) is adjustable. Note that FIG. 5 also shows the presence of Filters (F1). It is noted that Wavelengths for adjacent Orders overlap, and said Filters (F1) allow a user to pass only desired Wavelengths, as well as reduce background radiation entry to Photo Arrays (PA's). Typically a Focusing Element is not present in a FIG. 5 embodiment.

It is also noted that Fiber Optics can be utilized to carry Polychromatic Electromagnetic Radiation from a Source thereof (LS) to the position of a Polarizer (P), or from the position of an Analyzer (A) to a Detector (DET) in FIGS. 1–5.

Analogically similar figures to those shown in FIGS. 3–5, but oriented for use in a Transmission Mode are not shown, but should be understood as within the scope of the present invention as implied by FIG. 1.

Continuing, the present invention achieves a Spectroscopic Rotating Compensator Material System Investigation System (eg. Spectroscopic Rotating Compensator Ellipsometer System), preferably utilizing an "Off-The-Shelf" compact Spectrometer Systems, and utilizing "Off-The-Shelf" Compensator Components which are not at all "ideal", as regards Achromaticity. To put this into perspective, it is noted that to date, there is no known Spectroscopic Rotating Compensator Ellipsometer available in the market-place. It is believed that this is because it has previously been believed that to achieve such a System an Achromatic Rotating Compensator (RC) would be required. Such Compensators are not generally commercially available, hence, are expensive and reasonable approximations thereof typically must be individually fabricated. (Note, as described in Co-pending Patent application Ser. No. 08/618,820, a Dual-Rhomb Rotating Compensator (RC) which provides about seven (7%) percent variation in Retardation effected over a range of Wavelengths of approximately 2 to 14 microns, has been developed at the University of Nebraska. However, it is not clear that even the identified University of Nebraska Dual-Rohmb Rotating Compensator (RC) would operate "Achromatically" outside the identified range of wavelengths).

Figure 8A:
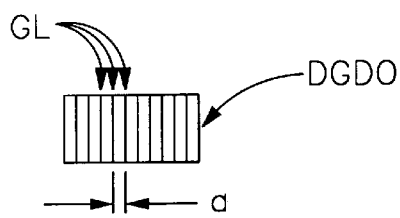
FIG. 8a shows lined diffraction grating dispersion optics geometry.
Figure 8B:
FIG. 8b shows a blazed angle lined diffraction grating dispersion optics geometry.
Figure 8C:
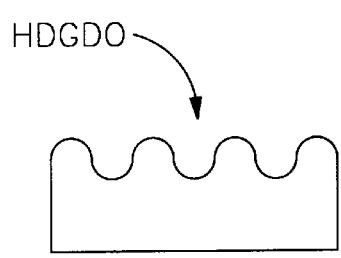
FIG. 8c shows a holographic lined diffraction grating dispersion optics geometry.
Figure 8D:
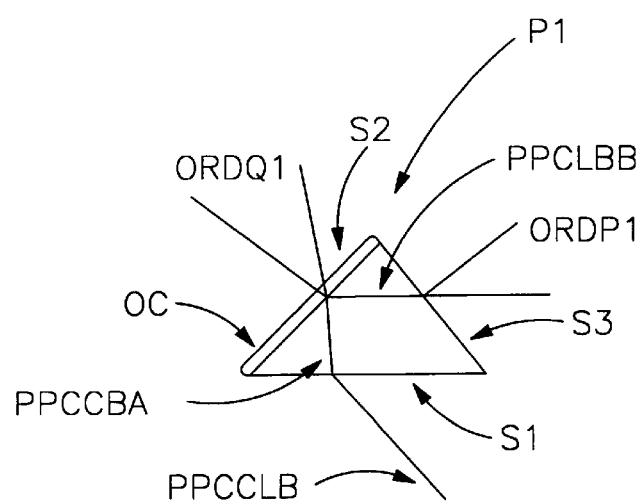
FIG. 8d shows a prism dispersion optics geometry.

For general information, FIGS. 8a through 8d show various Dispersive Optics geometries. FIG. 8a shows a lined geometry diffraction grating (DGDO). The grating lines (CL) are essentially rectangular in cross-section with a spacing (a) therebetween. FIG. 8b shows a "Blazed" geometry Diffraction Grating Dispersive Optics (BDGDO). The Blazing Angle (BA) shifts reflected diffracted energy between "Orders" such into +ORD1 and -ORD1 from a typically useless ORD0 which projects perpendicularly back from the surface of said Dispersive Optics shown in FIG. 5. FIG. 8c shows a cross-sectional view of a Holographic Diffraction Grating Dispersion Optics (HDGDO) as is present in the Off-the-Shelf (Zeiss Diode Array Spectrometer systems identified infra herein. Said Zeiss Systems utilize a Holographic configuration in a concave shaped system). FIG. 8d shows a Prism Dispersive Optics (P1), with a Polarized Polychromatic Electromagnetic Beam (PPCCLB) entering Side (S1), and exiting Side (S2) and Side (S3) as Diffracted Beams in two "Orders" (ORDQ1) and (ORDP1) respectively. Note that a coating (OC) causes partial internal reflection of beam (PPCCBA) into beam (PPCLBB) to produce two "Orders". Any functional Diffraction effecting element can be utilized as a Dispersive Optics (DO) in the present invention.

As the present invention can utilize Fiber Optics, certain geometries thereof are shown in FIGS. 9a through 9c. FIG. 9a shows a Fiber Optic which is essentially circular at the left side and which becomes of a "slit" shape at the right side. FIG. 9b shows a Fiber Optic which is essentially circular shaped along the entire length thereof, and which provides input to a "Slit" per se., (as is functionally utilized in the embodiment shown in FIG. 2). The effects achieved by the Fiber Optics in FIGS. 9a and 9b are similar. FIG. 9c shows a Trifrucated Fiber Optic which is essentially circular at the left side, which trifrucates and then is exemplified as becoming circular or a of a "slit" shape at the right side. Use of an effectively Trifrucated Fiber Optics is shown applied in FIG. 4. (Noted that present invention Optical Fibers are utilized only as convenient means by which to transport electromagnetic radiation and not to modify polarization state).

PRESENT INVENTION METHOD OF CALIBRATION (Note, the Calibration Method of the present invention is better described in the Disclosure of the Invention Section of this Specification. The following is to be considered as supplemental to the description provided in said Disclosure of the Invention Section).

In use, the present invention Spectroscopic Rotating Compensator Material System Investigation System is modeled mathematically, with Calibration Parameters being included in said Mathematical Model. Said Calibration Parameters are evaluated by a regression based approach based upon Data Set(s) obtained at a multiplicity of Angles-of-Incidence, and/or Wavelengths and/or Polarizer or Analyzer Rotation Angle Settings etc. (Note that a relatively easily obtained Two Dimensional Data Set as a function of Wavelength, and either Polarizer or Analyzer Azimuthal Angle Setting, is greatly preferred and has been found to be sufficient). As mentioned infra herein, typically, Matrix representations of the Polarizer (P), Compensator (C), Analyzer (A), are utilized, with calibration parameters appearing in Matrix Components. Once evaluation of the Spectroscopic Rotating Compensator Ellipsometer System (RC) Calibration Parameters is effected, a Material System (MS) can be subjected to investigation thereby, with otherwise unexplained changes effected in a Beam of Polarized Electromagnetic Radiation (LB), present after interaction with a Material System (MS), being attributed to said Material System (MS). (It is also to be noted that PSI and DELTA associated with a Material System at a specific Angle-Of-Incidence can be simultaneously evaluated with Calibration Parameter values if a Data Set is obtained utilizing a Material System present mode and the Mathematical Model includes said Material System PSI and DELTA as Fit Parameters).

Figure 6:
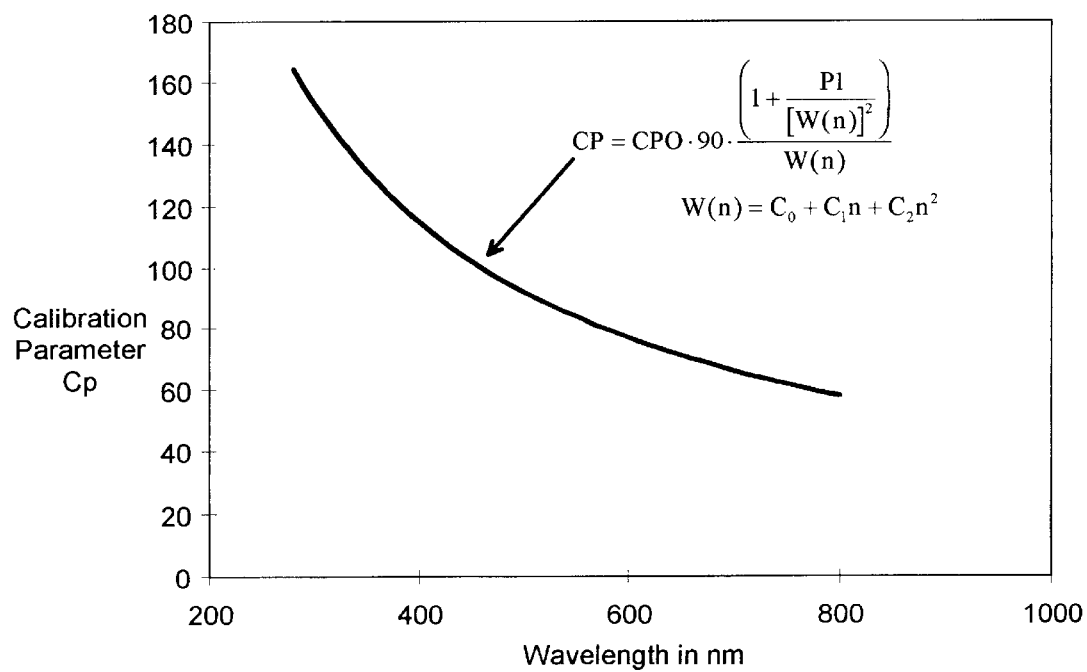
FIG. 6 demonstrates the Parameterization Approach to modeling Calibration Parameters which the present invention utilizes in certain cases.

FIG. 6 demonstrates a present invention "Parameterization" approach to modeling Calibration Parameters in a Mathematical Model. It must be understood that Calibration Parameters are often a function of Wavelength. For instance, the Retardation provided by a Compensator often varies inversely with wavelength. Where this is the case typical Mathematical Regression based evaluation of Calibration Parameters requires that a value for a Calibration Parameter be determined at each wavelength monitored. However, FIG. 6 shows that a plot of a Calibration Parameter vs. Wavelength can yield a locus which can be accurately modeled by a Mathematical Equation which requires only a few constants be known to allow calculation of the Calibration Parameter at a given Wavelength. For instance, FIG. 6 shows that a value for a Wavelength W(n) can be calculated knowing a Channel Number (n), (ie. Diode Element in an Array, such as shown in FIGS. 2–5), from which a signal is obtained, and values for three constants C0, C1 and C2. Knowing values for Parameters CP0 and P1 as well allows calculating a Calibration Parameter Value (CP) given a Diode Element Array Channel Number number (n). It can occur that (n) is two-hundred (200) or more and if a non-Parameterized approach to calibration is utilized, two-hundred (200) or more values for Calibration Parameter CP would have to be determined and stored. However, utilizing the Calibration Parameter Parameterization approach, it can be seen that a Regression procedure must return values for only Two (2) variables, (CP0 and P1). Also, if a Calibration Procedure were selected to include Angle-Of-Incidence (AOI) as a Data Set variable, it is known that where a Calibration Procedure utilizes a "Material System Present" configuration for acquiring data, that the PSI and DELTA values for the Material System will vary with said (AOI). (Note, said PSI and DELTA are equivalent to Calibration Parameters in a Regression procedure which serves to evaluate Calibration Parameters based upon Data obtained with a Material System present approach). A similar Parameterization approach could be applied to provide equations for calculating a PSI and a DELTA value given an (AOI), each of said equations involving only a few variables which would have to be evaluated by a Regression procedure. (Note, the concept of "Parameterization" is often encountered in the modeling of Dielectric Functions, wherein one or more Lorentz Oscillator(s) is/are utilized. Lorentz Oscillator Structures require only a Magnitude and a Broadening Calibration Parameter be evaluated to be fully defined. Some peak regions of a Dielectric Function can be adequately modeled by said two evaluated Calibration Parameters, however, the peak and tail regions of a Lorentz Oscillator Structure are not mathematically separate and while a Lorentz Oscillator Structure might adequately define a peak region in a Dielectric Function plot, it is often inadequate in non-peak regions. This problem is the focus in Co-pending Patent application Ser. No. 08/514,959 which teaches Finite Width Oscillator Structures comprised of Finite Order Polynomials and/or Finite Magnitude Essentially Zero Width Discontinuities as replacement for Lorentz Oscillator Structures). The present invention, where beneficial, utilizes Parameterization of Calibration Parameters. That is, where a plot of a Calibration Parameter vs. a Data Set Independent Variable demonstrates that Parameterization can be applied with benefit, the present invention Parameterization of Calibration Parameter approach, with respect to some Data Set Independent Variable, can be applied.

The present invention is then a Spectroscopic Rotating Compensator Material System Investigation System comprised of Components as identified in FIGS. 1–5, and the present invention is a Calibration Method which utilizes Regression, including Parameterization of Calibration Parameter where desired and beneficial, to evaluate Calibration Parameters in a Mathematical Model of said Spectroscopic Rotating Compensator Material System Investigation System.

PRESENT INVENTION APPLICATIONS RESULTS

In that the results obtained with the present invention Spectroscopic Rotating Compensator Material System Investigation System are considered to be quite impressive, (emphasis added), numerous examples of application of the present invention Spectroscopic Rotating Compensator Material System Investigation System are provided herein in the form of FIGS. 10a through 14h, which Figures show results of calibration, and data acquisition. It is noted that Calibration approaches "(GRM) 1" which utilizes Eqs. 45–47; "(GRM) 2" which utilizes Eq. 48; and "(GRM) 3" which utilizes Eq. 49, were all described in the Disclosure of the Invention Section of this Specification. The reader is referred thereto for renewed insight.

Figure 10A:
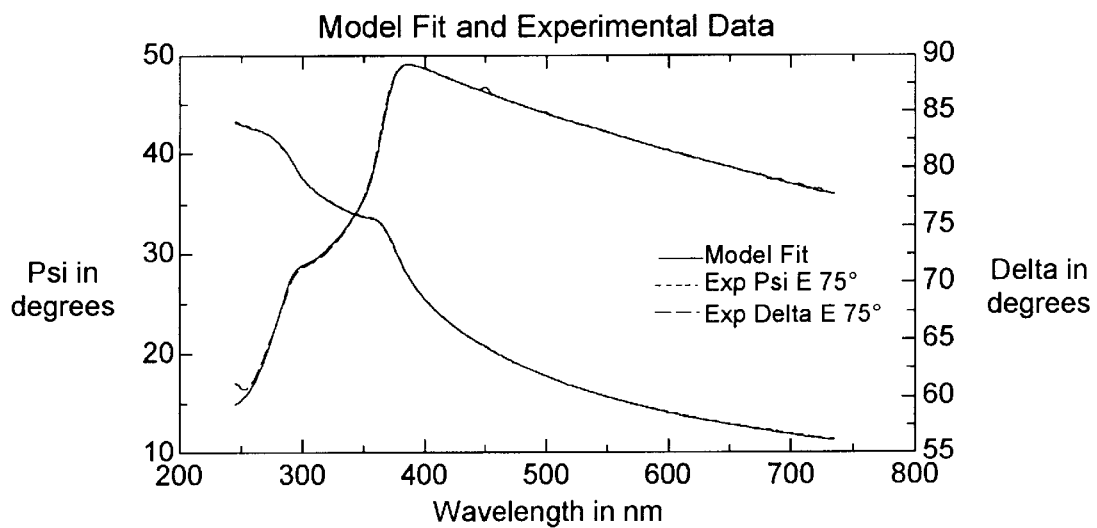
FIGS. 10a–10g provide graphically presented data pertaining to use of a Berek-type Compensator in a present invention Spectroscopic Rotating Compensator Material System Investigation System.
Figure 10B:
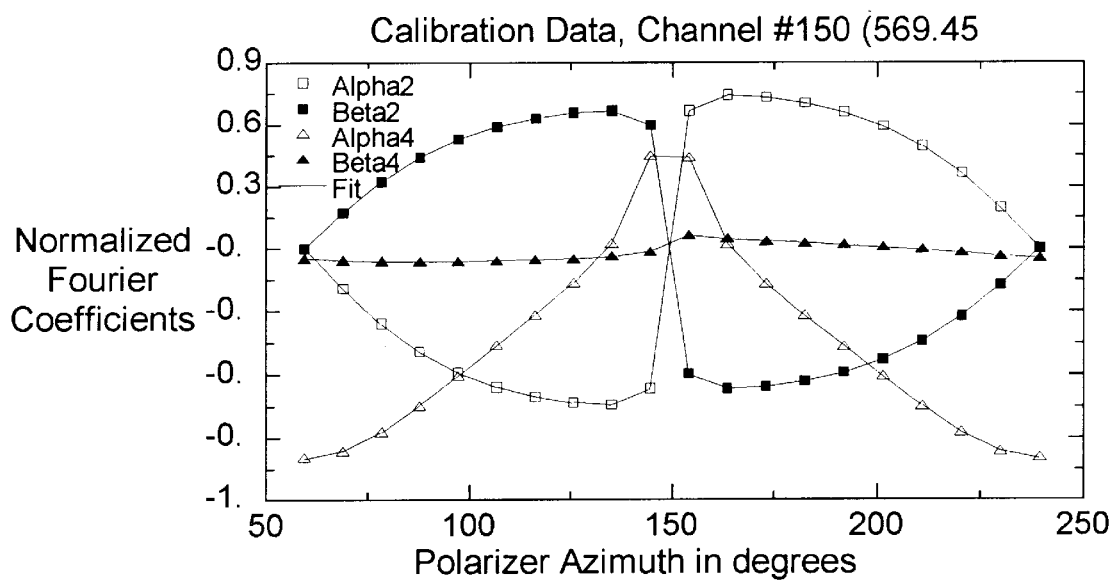

FIG. 10a shows PSI and DELTA results generated from a Silicon Dioxide on Silicon Sample Material System, which results were obtained with a present invention Spectroscopic Rotating Compensator Material System Investigation System when a Magnesium Fluoride Berek-type Compensator was utilized as the Rotating Compensator, positioned after said Material System. It is noted that Magnesium Fluoride has a wide spectral range, extending from the deep UV to the Mid IR, and is not Optically Active. It is noted that the Berek-type Compensator was tipped approximately five (5) degrees so that the polarized electromagnetic beam provided by the present invention Spectroscopic Rotating Compensator Material System Investigation did not approach the Berek-type Compensator along the Optical Axis. It is noted that the Berek-type Compensator utilized was approximately two (2) milimeters thick, and provided retardation of from one-hundred-sixty (160) degrees to sixty (60) degrees over a range of Wavelengths of from two-hundred-forty-five (245) to seven-hundred-thirty-five (735) nanometers. To obtain FIG. 10a a (GRM) 1 Calibration procedure was followed which, in addition to the FIG. 10a plot, provided the following results:

FIG. 10b shows that the "(GRM) 1" fit between Predicted and Experimentally determined Fourier Data is excellent, where Eq. 35c normalization was applied.

Figure 10C:
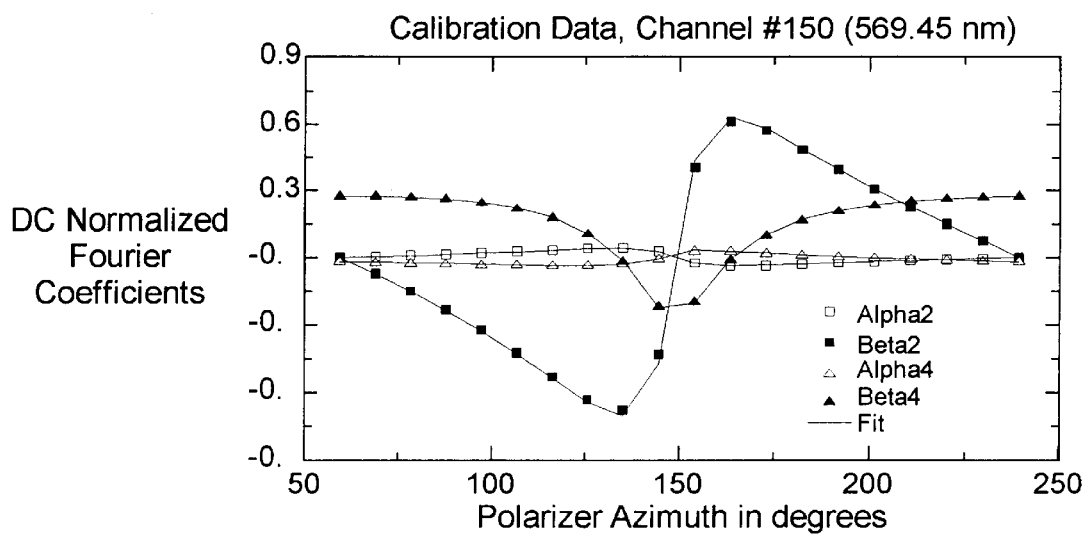

FIG. 10c shows that the "(GRM) 1" fit between Predicted and Experimentally determined Fourier Data, where Eq. 35c normalization was applied. While the curve shapes are different than in FIG. 10b the fits are again excellent.

Figure 10D:
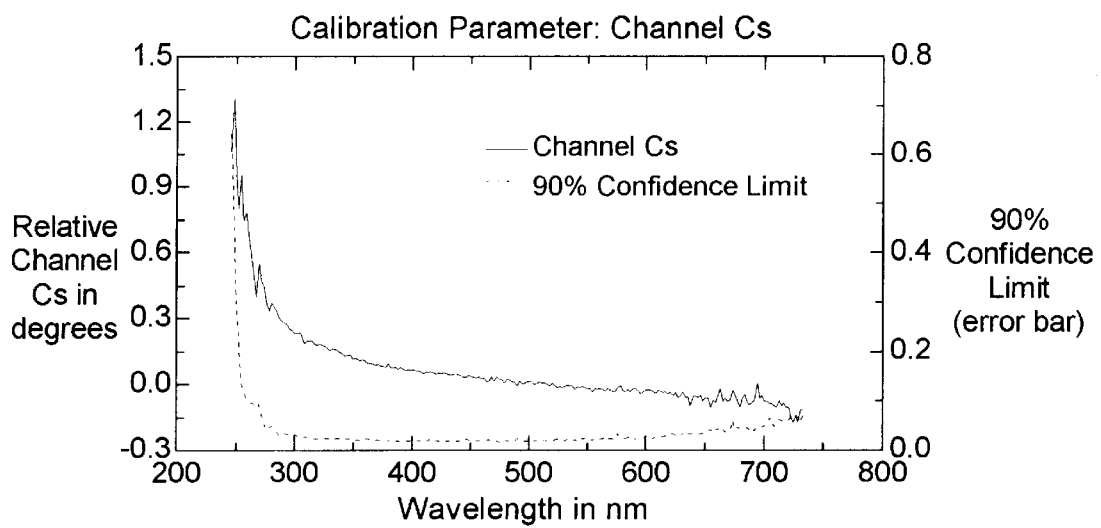
Figure 10E:
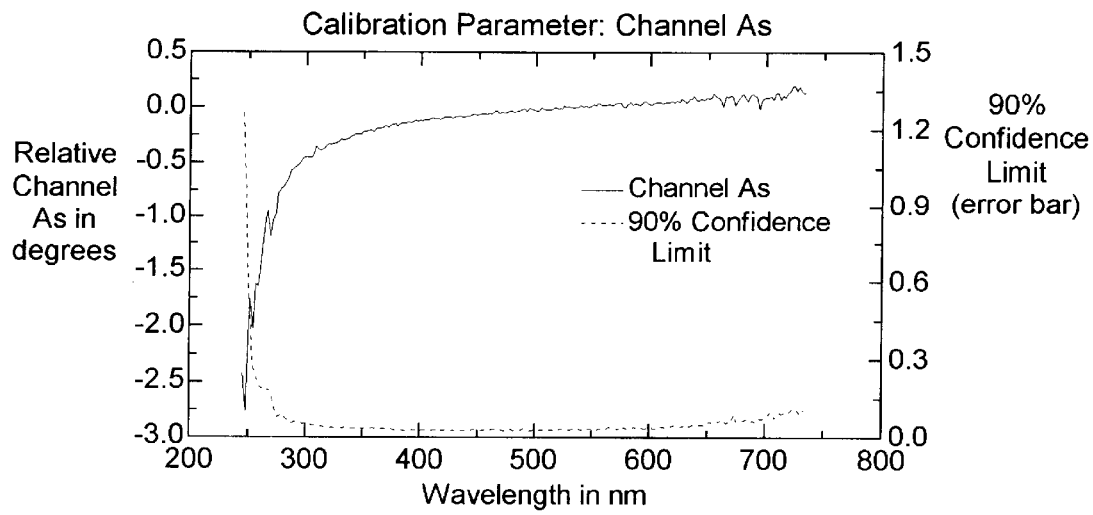
Figure 10F:
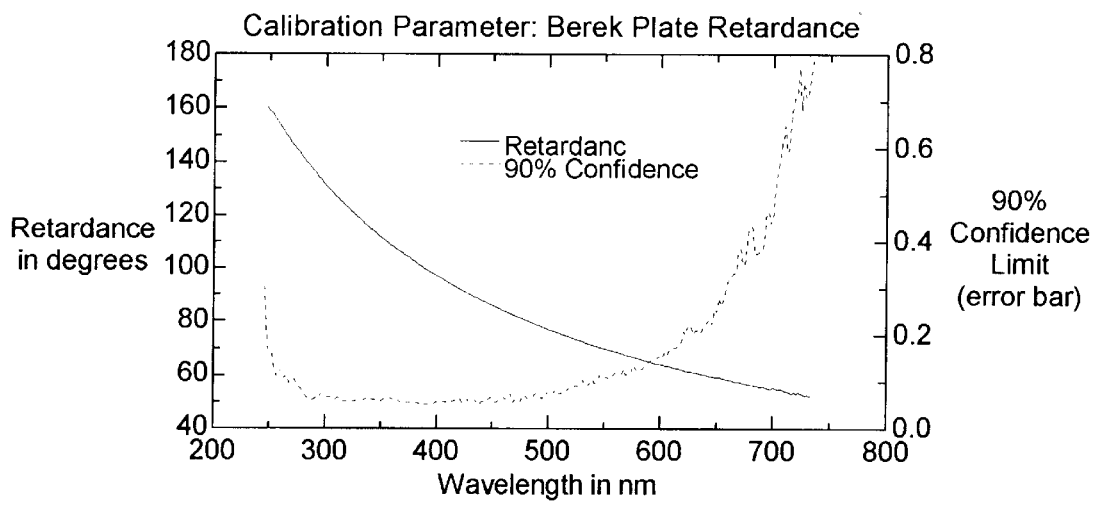

FIGS. 10d and 10e show (Cs)n and (As)n Calibration Parameters determined utilizing the "(GRM) 2" approach, which (Cs)n and (As)n Calibration Parameters were fit discretely for "n"'th Channels of the Photo Array. The plots in FIGS. 10d and 10e both exhibit fairly constant behavior across the spectrum, although there is a slight deviation of approximately one (1) degree in the UV part of the spectrum. FIG. 10f shows the Retardance of the Berek-type Compensator as a function of Wavelength. The dashed lines on the plots indicate a ninety (90) percent confidence limit value which is statistically determined from Levenberg-Marquardt non-linear regression analysis. This value is related to the precision and accuracy to which the Calibration Parameter vs. Wavelength can be determined.

Figure 10G:
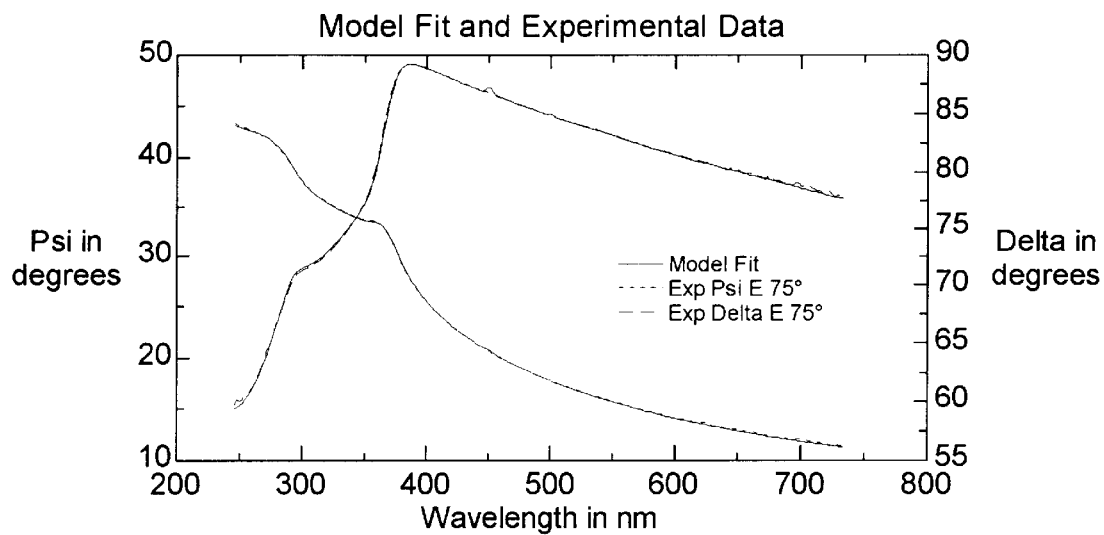

FIG. 10g further exemplifies and illustrates the accuracy of the present invention Spectroscopic Rotating Compensator Material System Investigation where calibration was performed utilizing "(GRM) 3". The PSI and DELTA curves are in excellent agreement with a simple Silicon Dioxide on Silicon model which uses reference Optical Constants.

Figure 11A:
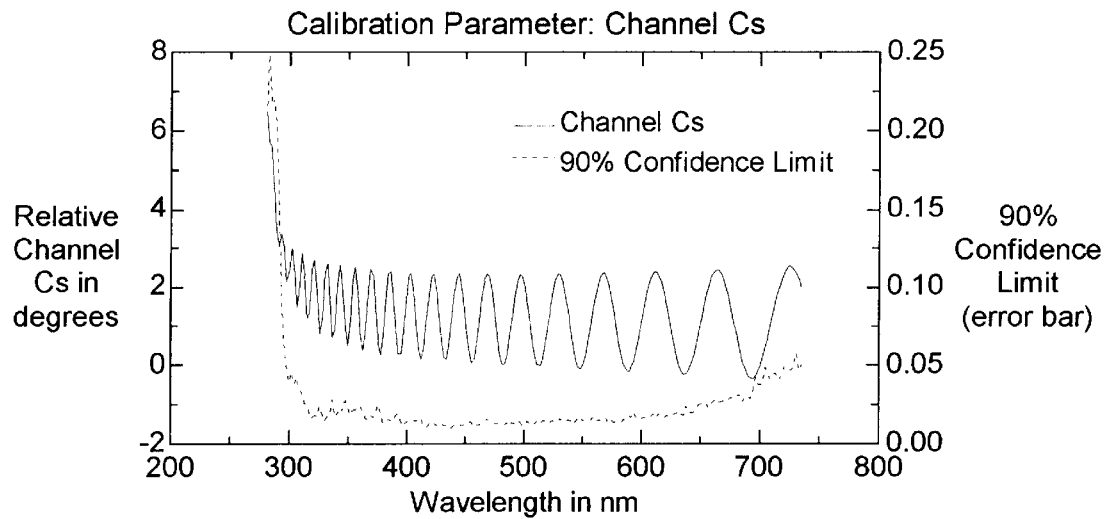
FIGS. 11a–11c provide graphically presented data pertaining to use of a Zero-Order Quarter Wave Plate Compensator in a present invention Spectroscopic Rotating Compensator Material System Investigation System.
Figure 11B:
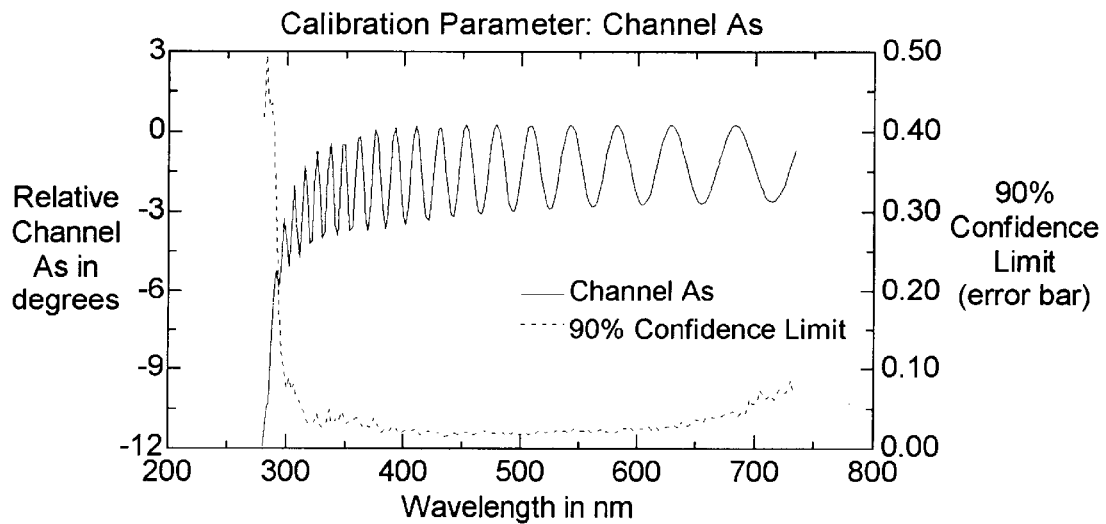
Figure 11C:
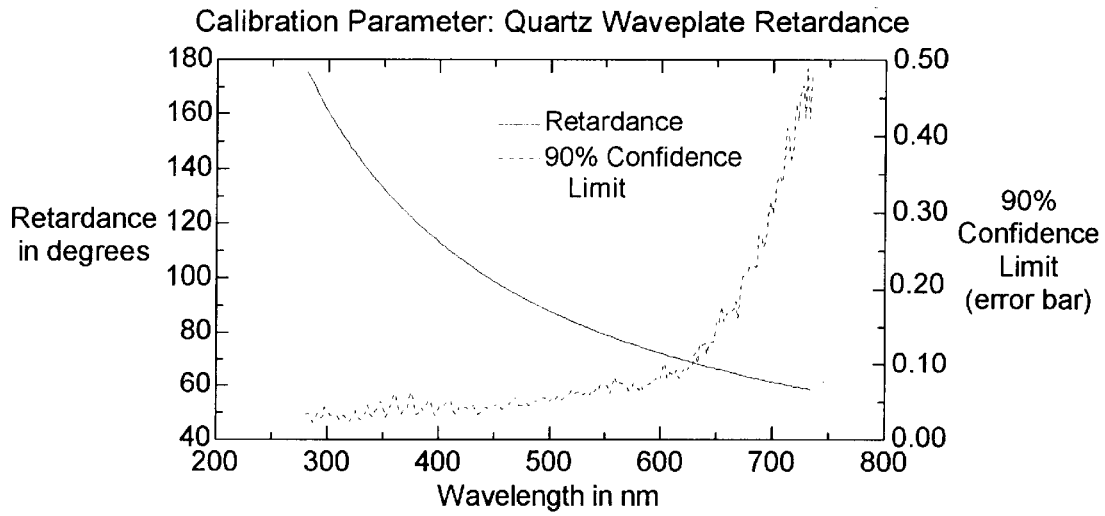

FIGS. 11a and 11b show (Cs)n and (As)n Calibration Parameter Fits for a case in which a Zero-Order Quartz Waveplate is utilized as the Compensator and in which a "(GRM) 2" approach is utilized. It is noted that where a Zero-Order Quartz Waveplate is utilized a "(GRM) 1" approach can not be practiced because the (As)n and (Cs)n Calibration Parameters are not constant as a function of Wavelength, but rather they "oscillate" as a function of Wavelength. FIG. 11c shows an expected inverse Retardance vs. Wavelength plot for the same Zero-Order Quartz Waveplate as is subject in FIGS 11a and 11b.

Figure 12A:
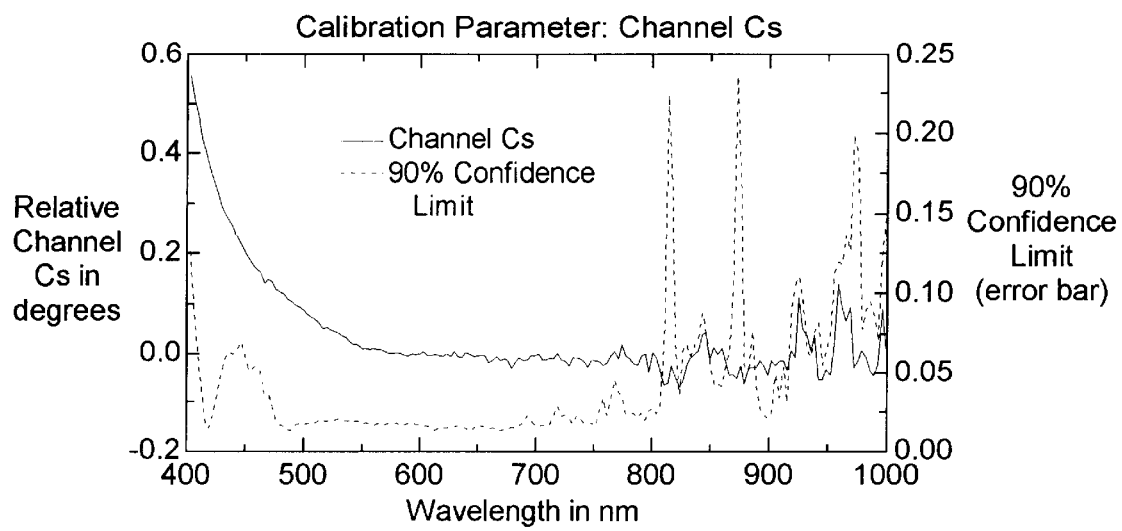
FIGS. 12a–12c provide graphically presented data pertaining to use of a Polymer Compensator in a present invention Spectroscopic Rotating Compensator Material System Investigation System.
Figure 12B:
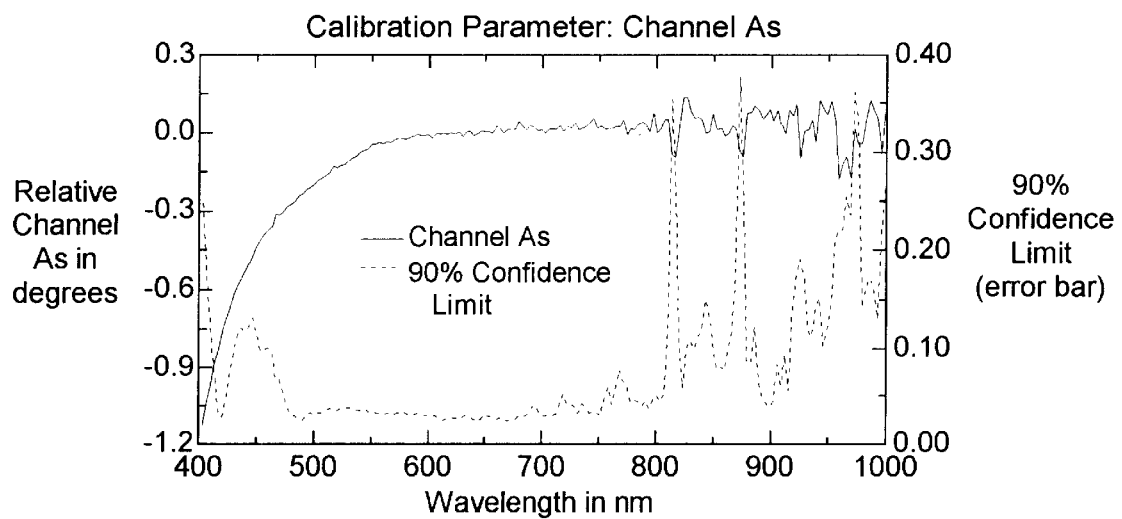
Figure 12C:
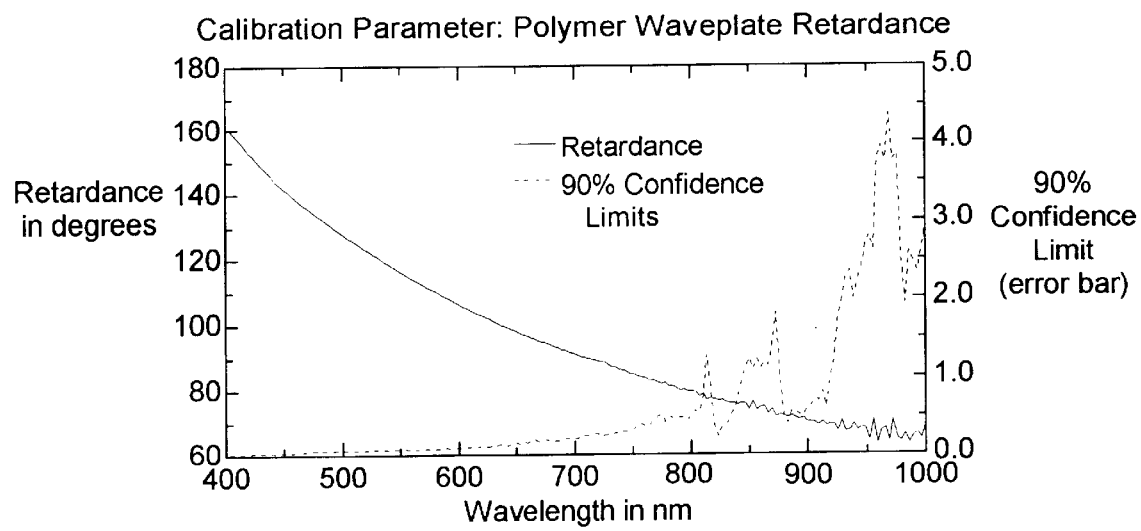

FIGS. 12a–12c show (Cs)n and (As)n Calibration Parameters and Retardance vs. Wavelength respectively, for a Polymer Compensator. While any of the various "(GRM) 1", "(GRM) 2)" and "(GRM) 3)" approaches can be utilized in calibration, the plots in FIGS. 12a–12c were obtained utilizing "(GRM) 3)".

Figure 13A:
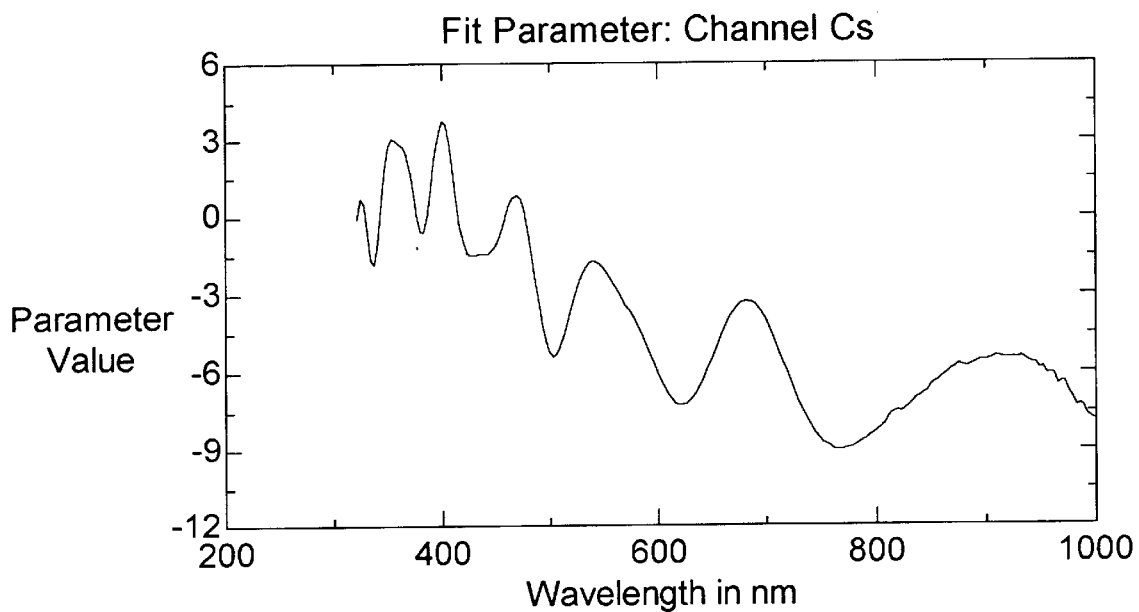
FIGS. 13a–13f provide graphically presented data pertaining to use of an "Achromatic" Waveplate Compensator in a present invention Spectroscopic Rotating Compensator Material System Investigation System.
Figure 13B:
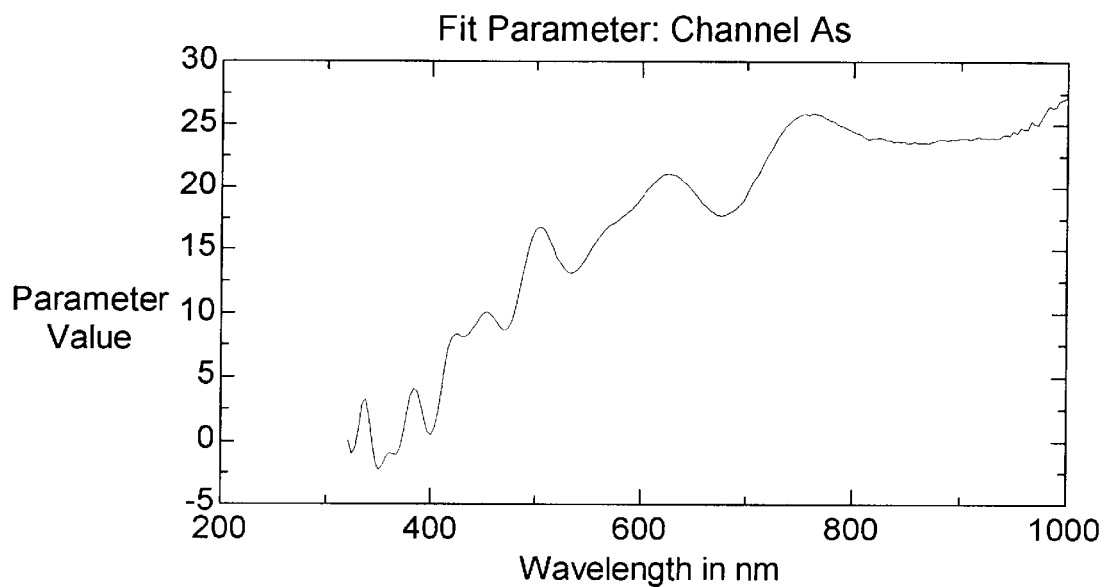
Figure 13C:
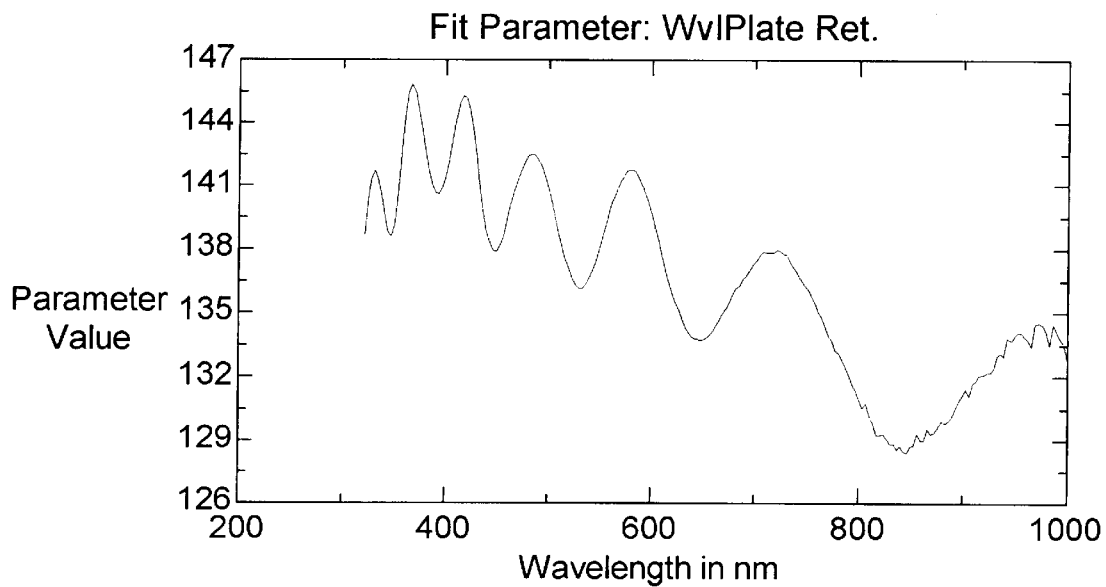
Figure 13D:
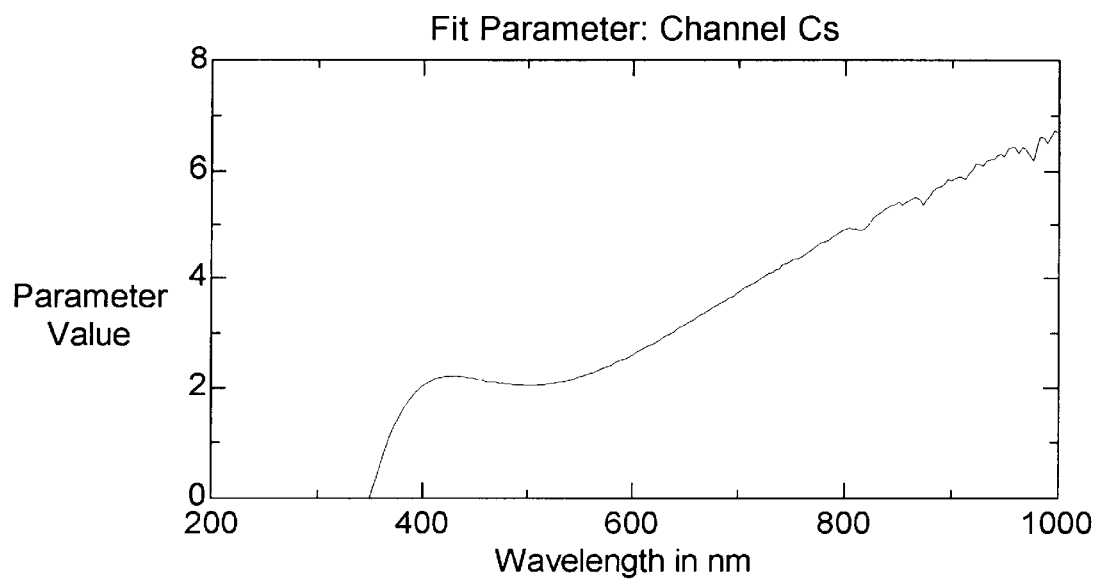
Figure 13E:
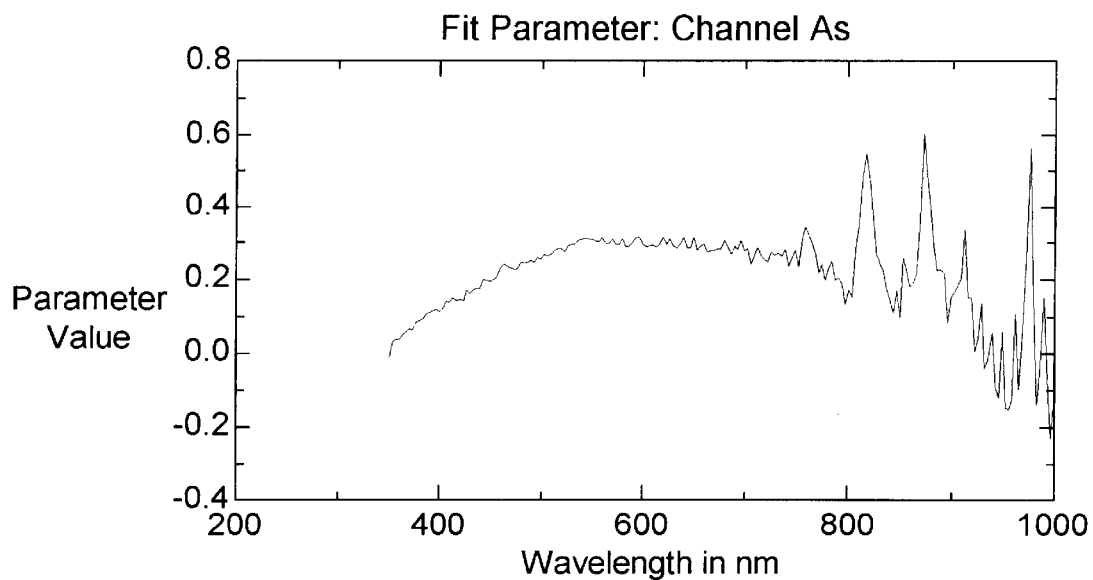
Figure 13F:
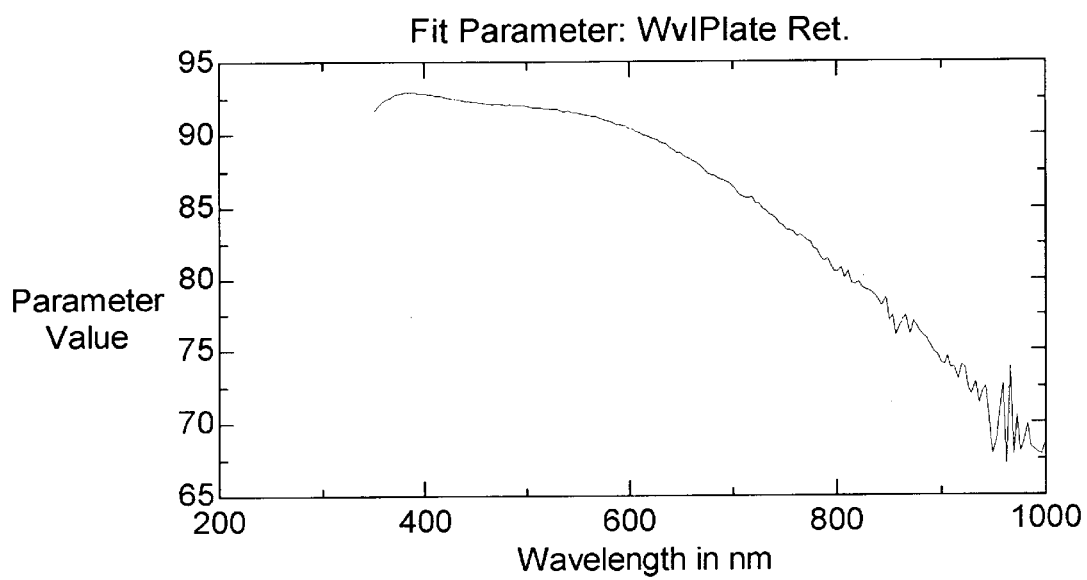

FIGS. 13a–13c show (Cs)n and (As)n Calibration Parameters and Retardance vs. Wavelength respectively, for an Achromatic Crystal Compensator. FIGS. 13d–13f show (Cs)n and (As)n Calibration Parameters and Retardance vs. Wavelength respectively, for an Achromatic Polymer Compensator. It is noted that "(GRM) 3" must typically be utilized to calibrate said Achromatic Compensators as system parameters do not lend well to Parameterization. It is to be noted that even in view of somewhat random behavior in system Calibration parameters, accurate ellipsometric data could still be acquired.

Figure 7:
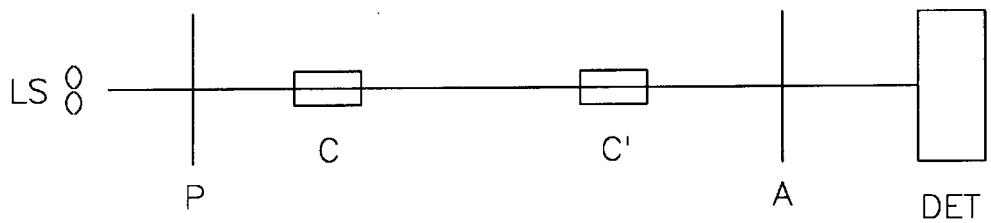
FIG. 7 demonstrates a "Straight-through" configuration of a Spectroscopic Rotating Compensator Material System Investigation System.
Figure 14A:
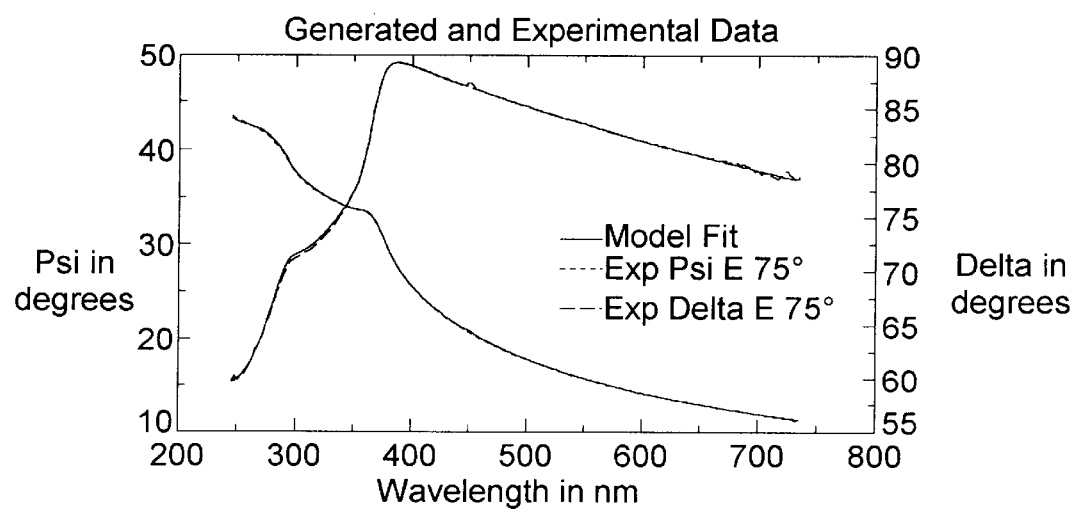
FIGS. 14a–14h provide graphically presented data for various measured material system PSI and DELTA values obtained using a present invention Spectroscopic Rotating Compensator Material System Investigation System.
Figure 14B:
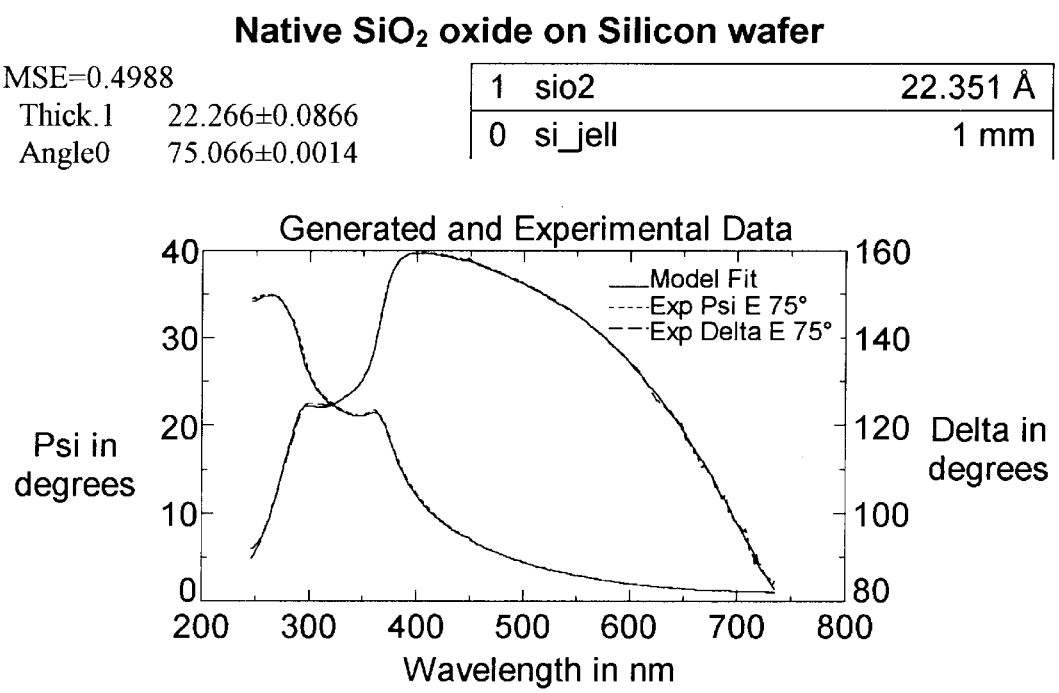
Figure 14C:
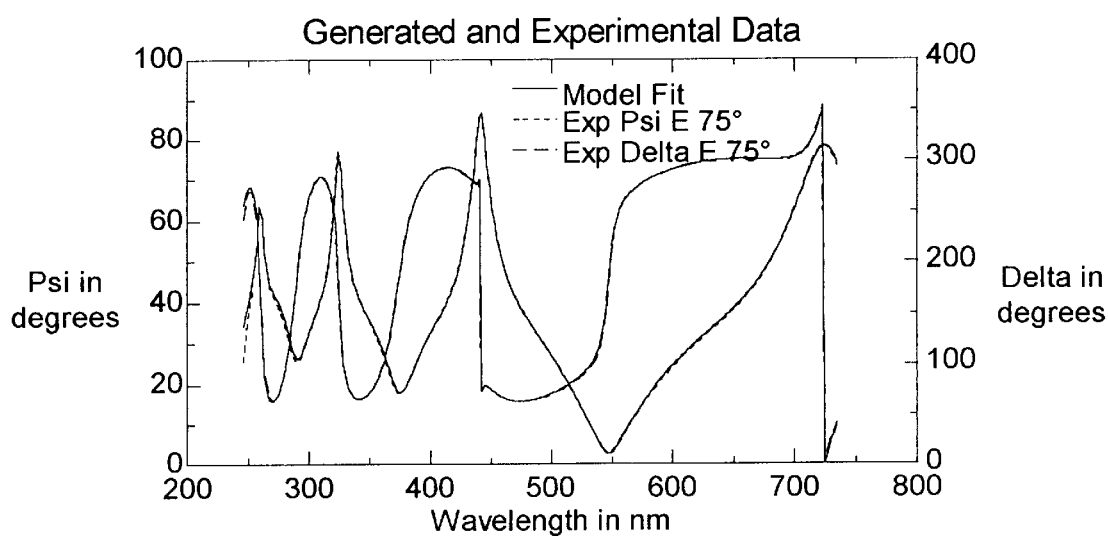
Figure 14D:
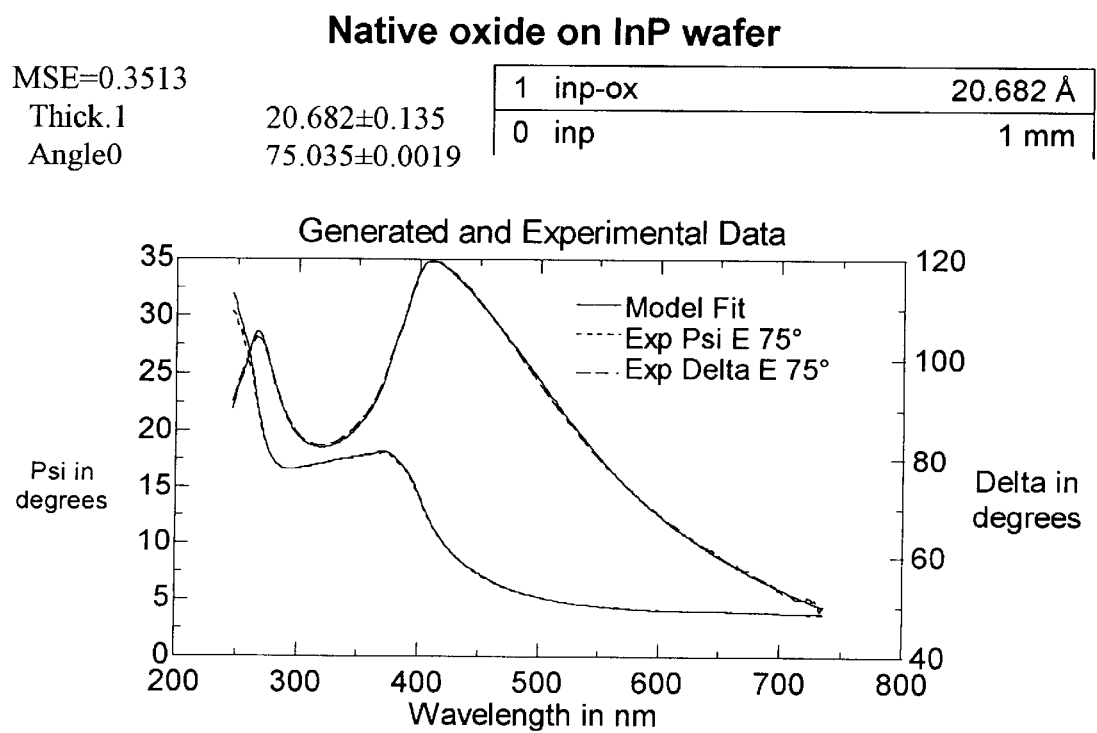
Figure 14E:
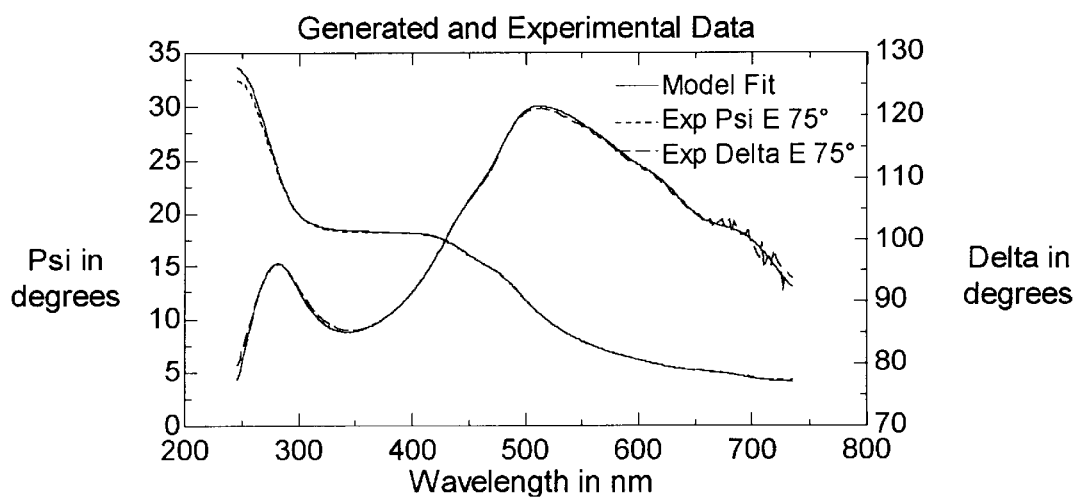
Figure 14F:
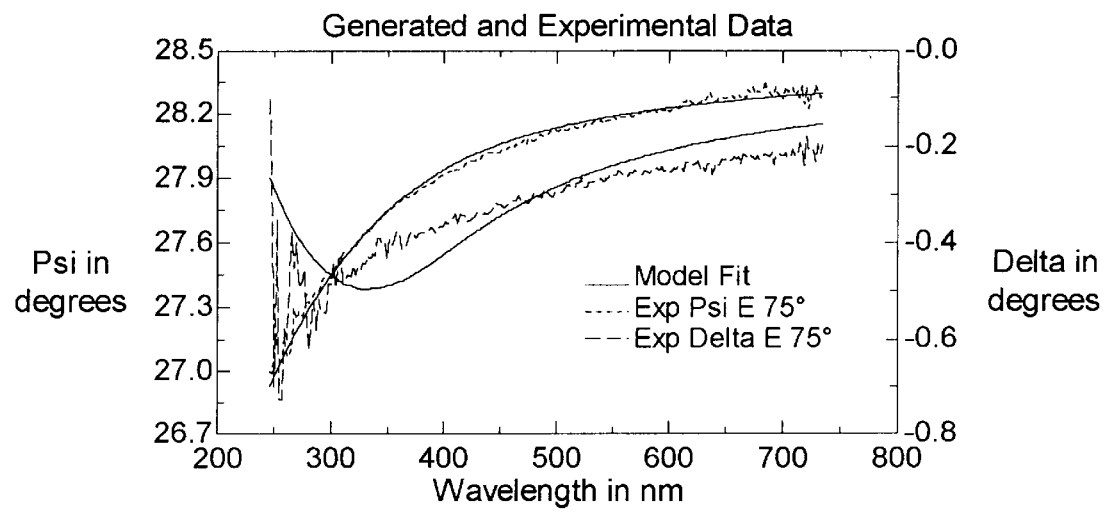
Figure 14G:
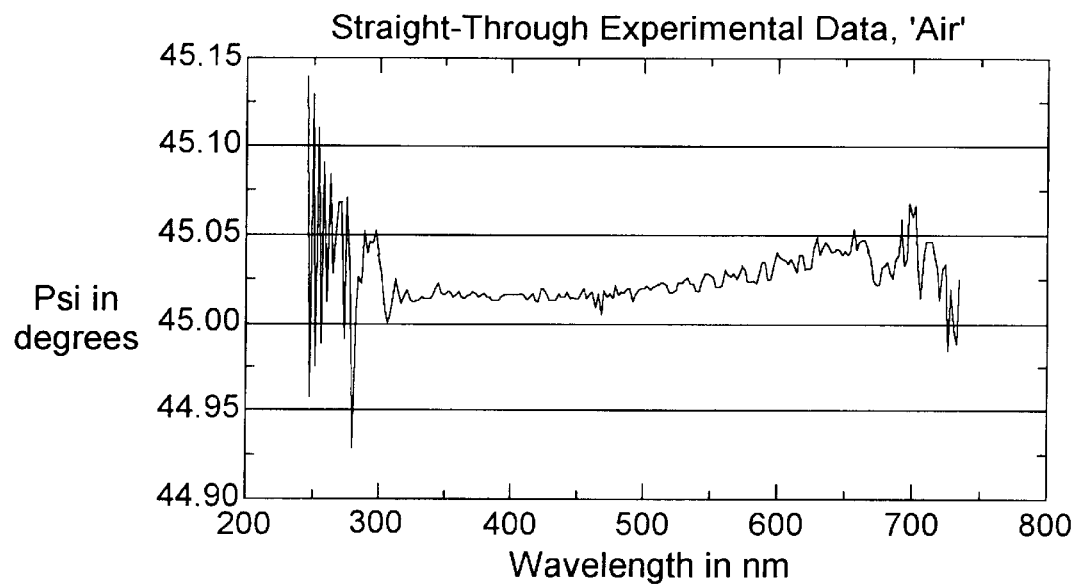
Figure 14H:
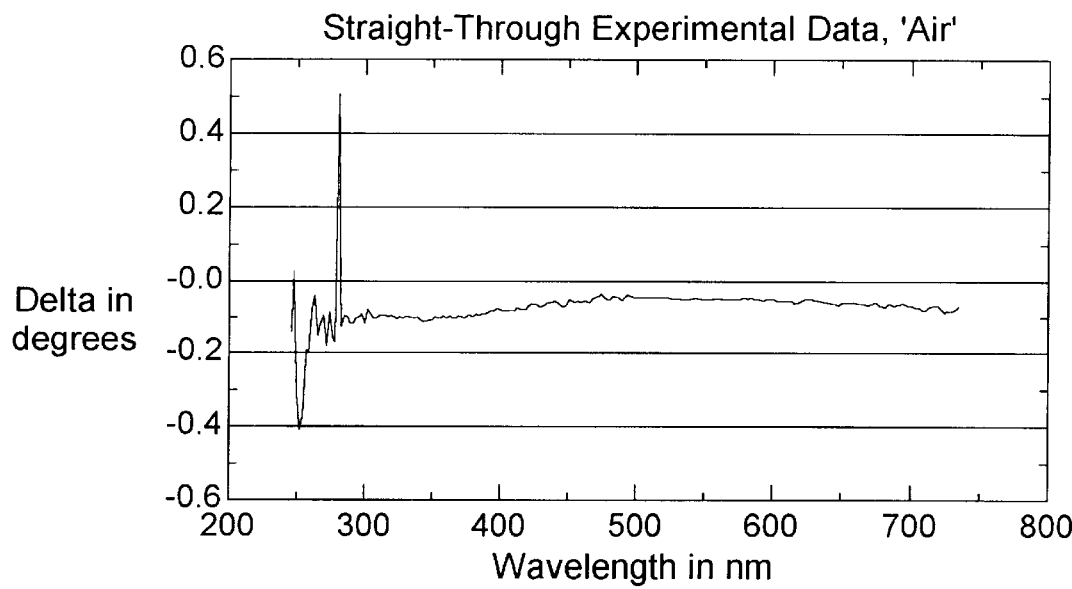

FIGS. 14a–14h show data acquired with a present invention Spectroscopic Rotating Compensator Material System Investigation System after it has been Calibrated for use. The data obtained is essentially equivalent regardless of what Compensator type is utilized. FIG. 14a shows PSI and DELTA values for thermal silicon Dioxide on a Silicon Substrate. FIG. 14b shows PSI and DELTA values for native silicon Dioxide on a Silicon Substrate. FIG. 14c shows PSI and DELTA values for thick TEOS on a Silicon Substrate. FIG. 14d shows PSI and DELTA for Native Oxide on an Indium Phosphide (InP) Wafer. FIG. 14e shows PSI and DELTA for Indium Gallium Arsenide (InGaAs) on an Indium Phosphide (InP) Wafer. FIG. 14f shows PSI and DELTA for Optically Flat Fused Silica. Finally, FIGS. 14g and 14h show, respectively, PSI and DELTA for "Air". That is, the present invention Spectroscopic Rotating Compensator Material System Investigation System was aligned in a "Straight-Through" configuration as shown in FIG. 7, (with Compensator (C) removed), and data obtained. Air is known to present with a PSI of forty-five (45) Degrees, and a DELTA of Zero (0.0) Degrees. FIG. 14g shows that said PSI of "Air" was determined to approximately Five-one-hundredths (0.05) Degree, and FIG. 14h shows that the DELTA of "Air" was determined to approximately One-tenth (0.1) Degree, over a range of Wavelengths beginning at approximately 300 nano-meters, and ending at approximately 700 nanometers. FIGS. 7, 14g and 14h serve to show that open atmosphere can be considered to be a Material System and that a polychromatic electromagnetic beam can be considered as being incident thereupon at an effective "Normal" Angle-of-Incidence, and transmitted therethrough.

In FIGS. 14a–14h it evident that various additional parameters (MSE—Mean-Square-Error provided by application of Regression fitting procedure); (Angle0—Angle-Of-Incidence of electromagnetic beam to Material System Surface while data was obtained); (Thickness—Thickness of surface layer), are provided. Also shown are Diagramatic Models of the Material Systems investigated, for which the PSI and DELTA are graphically presented. Said additional parameters are provided by the J. A. Woollam Co. Inc. WVASE, (Registered Trademark), Computer Program, when providing said Material System PSI and DELTA. The WVASE Reference Manual provides description of the additional parameters and said WVASE Reference Manual is incorporated herein by reference.

It is noted that the terminology Spectroscopic Rotating Compensator Material System Investigation System is to be interpreted sufficiently broadly to include Ellipsometers and Polarimeters and the like systems. In the claims the terminology Spectroscopic Rotating Compensator Material System Investigation System is utilized as being generic, with this in mind.

As well, it should be understood that a Mathematical Model developed to represent a present invention Spectroscopic Rotating Compensator Material System Investigation System can be expressed as explicit equations for Intensity Transfer Function, or as equations for Coefficients of Terms which comprise such as a Transfer Function. However, in the context of performing Regression based evaluation of Calibration Parameters, it is to be understood that a Mathematical Model can "Effectively" provide such equations. That is, a computer program need not calculate a Transfer Function per se. to utilize mathematical relationships inherrant therewithin. The terminology "Mathematical Model" and "Transfer Function, and "Coefficients of Terms" are to be interpreted sufficiently broadly so as to include the case where acutal explicit equations therefore are not per se. generated, but where mathematical relationships inherrant "Mathematical Model" and "Transfer Function, and "Coefficients of Terms" are utilized by a Regression based Calibration Parameter evaluation procedure. For instance, Numerical Equivalents to Specific Analytical Functions can be present and utilized in a Computer and be within the scope of the identified terminology, even though specific Analytical Equations are not per se., but only effectually, produced.

It is also to be appreciated that no other Spectroscopic Rotating Compensator Material System Investigation SYSTEM is known which comprises at once:

1. at least one non-Achromatic Characteristic Rotating Compensator (RC);
2. a Dispersive Optics (DO); and
3. a Detector Elements (DE's) containing Detector System (DET) which comprises a Photo Array (PA); such that in use a Multiplicity of Material System (MS)

Investigation Wavelengths in a Polychromatic Beam of Electromagnetic Wavelengths are simultaneously Monitored.

In particular, no known Spectroscopic Rotating Compensator Material System Investigation System utilizes a,(possibly Calibration Parameter Parameterization aided), Mathematical Regression based METHOD approach to Evaluation of Calibration Parameters in a Mathematical Model of such a Spectroscopic Rotating Compensator Material System Investigation System, such that application thereof allows compensating the Non-Achromatic, and other non-Ideal, aspects of a present Rotating Compensator.

It is emphasized that the present invention is considered to be particularly impressive as it is relatively easily constructed utilizing commercially available "Off-The-Shelf" Diode Array Spectrometer Systems, and non-ideal Compensators. The present invention conveniently provides, in a commercially realizable format, that which was thought to be, prior to the present invention, essentially impossibly to provide in other than a prohibitively expensive, (and perhaps difficult to calibrate and utilize), single unit format.

It is to be understood tha ta Photo Array can be comprised of Diode-Elements, Charge-Coupled-Devices, Bucket-Brigade-Devices and equivalents.

It is also noted that Polychromatic Electromagnetic Beam Source can be comprised of a combined plurality/multiplicity of Laser Sources, and that Polychromatic Electromagnetic Beam Source can include an effective Polarizer therewithin, thereby eliminating the need for a separate Polarizer. Such cases are to be considered within the scope of the claims.

It is also to be understood that the terminology "Achromatic" is to be understood to mean that an uncertainty in Retardance provided by a Compensator of One (1.0) Degree will effect an uncertainty of One-Quarter (¼) Degree in a measured Sample System (PSI), and an uncertainty of One-Half (½) Degree in a measured Sample System (DELTA), (as provided by Eq. 58 in the previously cited Kleim reference).

Having hereby disclosed the subject matter of this invention, it should be obvious that many modifications, substitutions and variations of the present invention are possible in light of the teachings. It is therefore to be understood that the present invention can be practiced other than as specifically described, and should be limited in breadth and scope only by the claims.

I claim:

1. A spectroscopic rotating compensator material system investigation system comprising a source of a polychromatic beam of electromagnetic radiation, a polarizer, a stage for supporting a material system, an analyzer, a dispersive optics and at least one detector system which contains a multiplicity of detector elements, said spectroscopic rotating compensator material system investigation system further comprising at least one compensator(s) positioned at a location selected from the group consisting of:

before said stage for supporting a material system; and after said stage for supporting a material system; and both before and after said stage for supporting a material system;

such that when said spectroscopic rotating compensator material system investigation system is used to investigate a material system present on said stage for supporting a material system, said analyzer and polarizer are maintained essentially fixed in position and at least one of said at least one compensator(s) is caused to continuously rotate while a polychromatic beam of electromagnetic radiation produced by said source of a polychromatic beam of electromagnetic radiation is caused to pass through said polarizer and said compensator(s), said polychromatic beam of electromagnetic radiation being also caused to interact with said material system, pass through said analyzer and interact with said dispersive optics such that a multiplicity of essentially single wavelengths are caused to simultaneously enter a corresponding multiplicity of detector elements in said at least one detector system.

2. A spectroscopic rotating compensator material system investigation system as in claim 1 in which dispersive optics and detector elements are commonly mounted with a beam splitting means, said beam splitting means serving to divert a portion of the polychromatic beam of electromagnetic radiation which otherwise proceeds to said dispersive optics, and transmit the remainder of said polychromatic beam of electromagnetic radiation toward said dispersive optics, said diverted portion of said polychromatic beam of electromagnetic radiation being directed by said beam splitting means into an alignment means selected from the group consisting of:

reticule; and electromagnetic beam detecting means;

combination with commonly mounted dispersive optics and detector elements orientation control means, such that in use said alignment means provides monitored alignment capability thereby allowing precise control of the locus of propagation of the portion of said polychromatic beam of electromagnetic radiation which passes through said beam splitting means, interacts with said dispersive optics, and enters said detector means.

3. A spectroscopic rotating compensator material system investigation system as in claim 1 in which dispersive optics and detector elements are contained in an off-the-shelf diode array spectrometer system.

4. A spectroscopic rotating compensator material system investigation system as in claim 3 in which said off-the-shelf diode array spectrometer system is manufactured by Zeiss and provides an operational wavelength range selected from the group consisting of:

300–1150 nm;

190–230 nm;

190–400 nm; and

900–2400 nm.

5. A spectroscopic rotating compensator material system investigation system as in claim 1 in which the compensator(s) is/are non-achromatic in that retardation effected thereby between quadrature components of a beam of electromagnetic radiation at one wavelength is different than that provided thereby at at least one other wavelength.

6. A spectroscopic rotating compensator material system investigation system as in claim 5 in which the non-achromatic compensator(s) presents with a retardance vs. wavelength characteristic essentially proportional to 1/wavelength.

7. A spectroscopic rotating compensator material system investigation system as in claim 1 in which the compensator(s) is/are achromatic in that retardation effected thereby between quadrature components of a beam of electromagnetic radiation at one wavelength is essentially the same as that provided thereby at other wavelengths.

8. A spectroscopic rotating compensator material system investigation system as in claim 1 in which said at least one of said at least one compensator(s) causes essentially no deviation or displacement in a polychromatic beam of electromagnetic radiation caused to pass therethrough while caused to rotate.

9. A spectroscopic rotating compensator material system investigation system as in claim 1 in which said at least one of said at least one compensator(s) is of a type selected from the group consisting of:
Berek-type with optical axis essentially perependicular to a surface thereof;
non-Berek-type with an optical axis essentially parallel to a surface thereof;
zero-order wave plate;
zero-order waveplate constructed from two multiple order waveplates;
rhomb;
polymer;
achromatic crystal; and
pseudo-achromatic.

10. A spectroscopic rotating compensator material system investigation system as in claim 1, in which the dispersive optics is a diffraction grating.

11. A spectroscopic rotating compensator material system investigation system as in claim 10 in which said diffraction grating is selected from the group consisting of:
a "lined";
a "blazed"; and
a "holographic" geometry;
said lined geometry consisting essentially of symetrical alternating lines with depressions therebetween, and said blazed geometry consisting of alternating ramp shaped lines with depressions therebetween, and said holographic geometry consisting of continuous cosine shaped lines and depressions.

12. A spectroscopic rotating compensator material system investigation system as in claim 1, in which the dispersive optics comprises a prism.

13. A spectroscopic rotating compensator material system investigation system as in claim 1 which further comprises a focusing element after said stage for supporting a material system and prior to said at least one detector system.

14. A spectroscopic rotating compensator material system investigation system as in claim 1 in which compensators are present both before and after said stage for supporting a material system, and a selection from the group consisting of:
both said compensators are caused to rotate in use; and
one of said compensators is caused to rotate in use;
is made.

15. A spectroscopic rotating compensator material system investigation system as in claim 1 in which a fiber optic is present at at least one location selected from the group consisting of:
between said source of a polychromatic beam of electromagnetic radiation and a polarizer; and
between said analyzer and said dispersive optics and at least one detector system which contains a multiplicity of detector elements.

16. A spectroscopic rotating compensator material system investigation system as in claim 15 in which a fiber optic is present after said analyzer, said fiber optic becoming at least bifrucated thereby providing a plurality of fiber optic bundles, at least two of which plurality of at least two bifrucated fiber optic bundles provide input to separate detector systems, each of said separate detector systems comprising a dispersion optics and a multiplicity of detector elements, said plurality of fiber optic bundles having cross-sectional shapes at ends thereof selected from the group:
essentially circular;
essentially slit shaped;
other than essentially circular; and
essentially slit shaped.

17. A spectroscopic rotating compensator material system investigation system as in claim 1 which is characterized by a mathematical model comprising calibration parameters which are members of the group consisting of:
polarizer azimuthal angle orientation;
present material system PSI;
present material system DELTA;
compensator azimuthal angle orientation(s);
matrix components of said compensator(s);
analyzer azimuthal angle orientation; and
detector element image persistence and read-out nonidealities;
which mathematical model is effectively a transfer function which enables calculation of electromagnetic beam intensity as a function of wavelength detected by a detector element, given intensity as a function of wavelength provided by said source of a polychromatic beam of electromagnetic radiation; said calibration parameters selected from the group consisting of:
polarizer azimuthal angle orientation;
present material system PSI;
present material system DELTA;
compensator azimuthal angle orientation(s);
matrix components of said compensator(s);
analyzer azimuthal angle orientation; and
detector element image persistance and read-out nonidealities);
being, in use, evaluated by performance of a mathematical regression of said mathematical model onto an at least two dimensional data set, said at least two dimensional data set being intensity values vs. wavelength and a parameter selected from the group consisting of:
angle-of-incidence of said polychromatic beam of electromagnetic radiation with respect to a present material system; and
azimuthal angle rotation of one element selected from the group consisting of:
said polarizer; and
said analyzer;
obtained over time, while at least one of said at least one compensator(s) is caused to continuously rotate.

18. A method of calibrating a spectroscopic rotating compensator material system investigation system comprising the steps of:
a. providing a spectroscopic rotating compensator material system investigation system comprising a source of a polychromatic beam of electromagnetic radiation, a polarizer, a stage for supporting a material system, an analyzer, a dispersive optics and at least one detector system which contains a multiplicity of detector elements, said spectroscopic rotating compensator material system investigation system further comprising at least one compensator(s) positioned at a location selected from the group consisting of:
before said stage for supporting a material system;
after said stage for supporting a material system; and
both before and after said stage for supporting a material system;

such that when said spectroscopic rotating compensator material system investigation system is used to investigate a material system present on said stage for supporting a material system, said analyzer and polarizer are maintained essentially fixed in position and at least one of said at least one compensator(s) is/are caused to continuously rotate while a polychromatic beam of electromagnetic radiation produced by said source of a polychromatic beam of electromagnetic radiation is caused to pass through said polarizer and said compensator(s), said polychromatic beam of electromagnetic radiation being also caused to interact with said material system, pass through said analyzer and interact with said dispersive optics such that a multiplicity of essentially single wavelengths are caused to simultaneously enter a corresponding multiplicity of detector elements in said at least one detector system;

b. developing a mathematical model of said spectroscopic rotating compensator material system investigation system which comprises as calibration parameter variables polarizer azimuthal angle orientation, present material system PSI, present material system DELTA, compensator azimuthal angle orientation(s), matrix components of said compensator(s), and analyzer azimuthal angle orientation, which mathematical model is effectively a transfer function which enables calculation of electromagnetic beam intensity as a function of wavelength detected by a detector element, given intensity as a function of wavelength provided by said source of a polychromatic beam of electromagnetic radiation;

c. causing a polychromatic beam of electromagnetic radiation produced by said source of a polychromatic beam of electromagnetic radiation, to pass through said polarizer, interact with a material system caused to be in the path thereof, pass through said analyzer, and interact with said dispersive optics such that a multiplicity of essentially single wavelengths are caused to simultaneously enter a corresponding multiplicity of detector elements in said at least one detector system, with said polychromatic beam of electromagnetic radiation also being caused to pass through said compensator(s) positioned at a location selected from the group consisting of:
  before said stage for supporting a material system;
  after said stage for supporting a material system; and
  both before and after said stage for supporting a material system;

d. obtaining an at least two dimensional data set of intensity values vs. wavelength and a parameter selected from the group consisting of:
  angle-of-incidence of said polychromatic beam of electromagnetic radiation with respect to a present material system; and
  azimuthal angle rotation of one element selected from the group consisting of:
    said polarizer; and
    said analyzer;
over time, while at least one of said at least one compensator(s) is caused to continuously rotate;

e. performing a mathematical regression of said mathematical model onto said at least two dimensional data set, thereby evaluating calibration parameters in said mathematical model;

said regression based calibration procedure evaluated calibration parameters serving to compensate said mathematical model for non-achromatic characteristics and non-idealities of said compensator(s), and for azimuthal angles of said polarizer, analyzer compensator(s).

19. A method of calibrating a spectroscopic rotating compensator material system investigation system as in claim 18 which further comprises including calibration parameters for detector element image persistance and read-out nonidealities in the mathematical model, and further evaluating said calibration parameters for detector element image persistance and read-out nonidealities in said regression procedure.

20. A method of calibrating a spectroscopic rotating compensator material system investigation system as in claim 18 in which the step of developing a calibration parameter containing mathematical model of said spectroscopic rotating compensator ellipsometer system includes the steps of providing a matrix representation of each of said polarizer, present material system, said compensator(s), and said analyzer, and determining a mathematical transfer function relating electromagnetic beam intensity cut to intensity in, as a function of wavelength, by multiplication of said matrices in a spectroscopic rotating compensator material system investigation system element presence representing order.

21. A method of calibrating a spectroscopic rotating compensator material system investigation system as in claim 18, which further comprises the step of parameterizing calibration parameters by representing variation as a function of a member of the group consisting of:
  wavelength;
  angle-of-incidence of said polychromatic beam of electromagnetic radiation with respect to a present material system; and
  azimuthal angle orientation of one element selected from the group consisting of:
    said polarizer; and
    said analyzer;
by a parameter containing mathematical equation, said parameters being evaluated during said mathematical regression.

22. A method of calibrating a spectroscopic rotating compensator material system investigation system as in claim 21, in which calibration parameters which are parameterized are selected from the group consisting of:
  polarizer azimuthal angle orientation;
  compensator azimuthal angle orientation;
  matrix components of said compensator(s); and
  analyzer azimuthal angle orientation;
each as a function of wavelength.

23. A method of calibrating a spectroscopic rotating compensator material system investigation system as in claim 18 in which the material system is selected from the group consisiting of:
  open atmosphere with the spectroscopic rotating compensator material system investigation system being oriented in a "straight-through" configuration; and
  other than open atmosphere with the spectroscopic rotating compensator material system investigation system being oriented in a "material-present" configuration.

24. A method of calibrating a spectroscopic rotating compensator material system investigation system comprising the steps of:
  a. providing a spectroscopic rotating compensator material system investigation system comprising a source of a polychromatic beam of electromagnetic radiation, a polarizer, a stage for supporting a material system, an analyzer, a dispersive optics and at least one detector system which contains a multiplicity of detector elements, said spectroscopic rotating compensator material system investigation system further comprising at least one compensator(s) positioned at a location selected from the group consisting of:

before said stage for supporting a material system;
after said stage for supporting a material system; and
both before, and after said stage for supporting a material system;

such that when said spectroscopic rotating compensator material system investigation system is used to investigate a material system present on said stage for supporting a material system, said analyzer and polarizer are maintained essentially fixed in position and at least one of said at least one compensator(s) is/are caused to continuously rotate while a polychromatic beam of electromagnetic radiation produced by said source of a polychromatic beam of electromagnetic radiation is caused to pass through said polarizer and said compensator(s), said polychromatic beam of electromagnetic radiation being also caused to interact with said material system, pass through said analyzer and interact with said dispersive optics such that a multiplicity of essentially single wavelengths are caused to simultaneously enter a corresponding multiplicity of detector elements in said at least one detector system;

b. developing a mathematical model of said spectroscopic rotating compensator material system investigation system which comprises as calibration parameter variables polarizer azimuthal angle orientation, present material system PSI, present material system DELTA, compensator azimuthal angle orientation(s), matrix components of said compensator(s), and analyzer azimuthal angle orientation, which mathematical model is effectively a transfer function which enables calculation of electromagnetic beam intensity as a function of wavelength detected by a detector element, given intensity as a function of wavelength provided by said source of a polychromatic beam of electromagnetic radiation, said mathematical model providing equations for coefficients of terms in said transfer function, said coefficients of terms each being a function of identified calibration parameters;

c. causing a polychromatic beam of electromagnetic radiation produced by said source of a polychromatic beam of electromagnetic radiation, to pass through said polarizer, interact with a material system caused to be in the path thereof, pass through said analyzer, and interact with said dispersive optics such that a multiplicity of essentially single wavelengths are caused to simultaneously enter a corresponding multiplicity of detector elements in said at least one detector system, with said polychromatic beam of electromagnetic radiation also being caused to pass through said compensator(s) positioned at a location selected from the group consisting of:

before said stage for supporting a material system;
after said stage for supporting a material system; and
both before and after said stage for supporting a material system;

d. obtaining an at least two dimensional data set of intensity values vs. wavelength and a parameter selected from the group consisting of:

angle-of-incidence of said polychromatic beam of electromagnetic radiation with respect to a present material system; and azimuthal angle rotation of one element selected from the group consisting of:
said polarizer; and
said analyzer;

over time, while at least one of said at least one compensator(s) is caused to continuously rotate and from said data set calculating numerical values for coefficients of terms in the transfer function for said spectroscopic rotating compensator material system investigation system;

e. performing a mathematical regression of said mathematical model equations for coefficients of terms in said transfer function, onto said transfer function term coefficient values, thereby evaluating said calibration parameters;

said regression based calibration procedure evaluated calibration parameters serving to compensate said mathematical model for non-achromatic characteristics and non-idealities of said compensator(s), and for azimuthal angles of said polarizer, analyzer compensator (s).

25. A method of calibrating a spectroscopic rotating compensator material system investigation system as in claim 24 in which a Hadamard analysis approach is utilized in calculating numerical values for coefficients of terms in the transfer function for said spectroscopic rotating compensator material system investigation system.

26. A method of calibrating a spectroscopic rotating compensator material system investigation system as in claim 24 which further comprises including calibration parameters for detector element image persistance and read-out nonidealities in the mathematical model, and further evaluating said calibration parameters for detector element image persistence and read-out nonidealities in said regression procedure.

27. A method of calibrating a spectroscopic rotating compensator material system investigation system as in claim 24, in which the step of developing a calibration parameter containing mathematical model of said spectroscopic rotating compensator ellipsometer system includes the steps of providing a matrix representation of each of said polarizer, present material system, said compensator(s), and said analyzer, and determining a transfer function relating electromagnetic beam intensity out to intensity in, as a function of wavelength, by multiplication of said matrices in a spectroscopic rotating compensator material system investigation system element presence representing order.

28. A method of calibrating a spectroscopic rotating compensator material system investigation system as in claim 24 in which the step of calculating values of coefficients of terms in a transfer function from said data set involves calculating values of coefficients of a Fourier Series.

29. A method of calibrating a spectroscopic rotating compensator material system investigation system as in claim 24 which further comprises the step of parameterizing calibration parameters by representing variation as a function of a member of the group consisting of:

wavelength;
angle-of-incidence of said polychromatic beam of electromagnetic radiation with respect to a present material system; and
azimuthal angle orientation of one element selected from the group consisting of:
said polarizer; and
said analyzer;

by a parameter containing mathematical equation, said parameters being evaluated during said mathematical regression.

30. A method of calibrating a spectroscopic rotating compensator material system investigation system as in claim 29, in which calibration parameters which are parameterized are selected from the group consisiting of:

polarizer azimuthal angle orientation;

compensator azimuthal angle orientation(s);

matrix components of said compensator(s); and analyzer azimuthal angle orientation;

each as a function of wavelength.

31. A method of calibrating a spectroscopic rotating compensator material system investigation system as in claim 24 in which the material system is selected from the group consisiting of:

open atmosphere with the spectroscopic rotating compensator material system investigation system being oriented in a "straight-through" configuration; and other than open atmosphere with the spectroscopic rotating compensator material system investigation system being oriented in a "material-present" configuration.

32. A spectroscopic rotating compensator material system investigation system comprising a source of a polychromatic beam of electromagnetic radiation, a polarizer, a stage for supporting a material system, an analyzer, a dispersive optics and at least one detector system which contains a multiplicity of detector elements, said spectroscopic rotating compensator material system investigation system further comprising at least one compensator positioned at a location selected from the group consisting of:

before said stage for supporting a material system;

after said stage for supporting a material system; and before and after said stage for supporting a material system;

such that when said spectroscopic rotating compensator material system investigation system is used to investigate a material system present on said stage for supporting a material system, said analyzer and polarizer are maintained essentially fixed in position and at least one of said said at least one compensator(s) is caused to continuously rotate while a polychromatic beam of electromagnetic radiation produced by said source of a polychromatic beam of electromagnetic radiation is caused to pass through said polarizer and said compensator(s), said polychromatic beam of electromagnetic radiation being also caused to interact with said material system; said polychromatic beam of electromagnetic radiation being also, without further focusing, caused to pass through said analyzer and interact with said dispersive optics, said dispersive optics serving to form a plurality of essentially spacially offset orders when said polychromatic beam of electromagnetic radiation is caused to impinge thereupon, each said produced order comprising an essentially continuous spectrum of spacially separated electromagnetic beams of essentially single wavelengths, many of said essentially single wavelengths being present in two or more produced orders; such that in use first and second multiplicities of essentially single wavelength beams of electromagnetic radiation from first and second produced orders are simultaneously intercepted by, respectively, first and second detector systems, thereby enabling the simultaneous accessing of a first multiplicity of essentially single wavelengths by said first detector system and a second multiplicity of essentially single wavelengths by said second detector system, each of which first and second multiplicities of essentially single wavelengths intercepted by said first and second detector systems, respectively, includes specific first and second essentially single wavelength beams of electromagnetic radiation, said specific first and second essentially single wavelength beams of electromagnetic radiation being simultaneously intercepted by specific detector elements in said first and second detector systems respectively, even where electromagnetic beams of said specific first and second essentially single wavelengths are spacially situated to close to one another in a single produced order for separate photo detector array detector elements in a single detector system which intercepts said single order, to, simultaneously, access beams of electromagnetic radiation of both said specific first and second essentially single wavelengths, separately.

33. A spectroscopic rotating compensator material system investigation system as in claim 32 in which the compensator(s) is/are non-achromatic in that retardation effected thereby between quadrature components of a beam of electromagnetic radiation at one wavelength is different than that provided thereby at at least one other wavelength.

34. A spectroscopic rotating compensator material system investigation system as in claim 33 in which the non-achromatic compensator(s) presents with a retardance vs. wavelength characteristic essentially proportional to 1/wavelength.

35. A spectroscopic rotating compensator material system investigation system as in claim 32 in which the compensator(s) is/are achromatic in that retardation effected thereby between quadrature components of a beam of electromagnetic radiation at one wavelength is essentially the same as that provided thereby at other wavelengths.

36. A spectroscopic rotating compensator material system investigation system as in claim 32 in which said at least one of said at least one compensator(s) causes essentially no deviation or displacement in a polychromatic beam of electromagnetic radiation caused to pass therethrough while caused to rotate.

37. A spectroscopic rotating compensator material system investigation system as in claim 32 in which said at least one of said at least one compensator(s) is of a type selected from the group consisting of:

Berek-type with optical axis essentially perependicular to a surface thereof;

non-Berek-type with an optical axis essentially parallel to a surface thereof, zero-order wave plate;

zero-order waveplate constructed from two multiple order waveplates;

rhomb;

polymer;

achromatic crystal; and pseudo-achromatic.

38. A spectroscopic rotating compensator material system investigation system as in claim 32, in which the dispersive optics is a diffraction grating.

39. A spectroscopic rotating compensator material system investigation system as in claim 38, in which said diffraction grating is selected from the group consisting of a "lined", a "blazed", and a "holographic" geometry, said lined geometry consisting essentially of symetrical alternating lines with depressions therebetween, and said blazed geometry consisting of alternating ramp shaped lines with depressions therebetween, and said holographic geometry consisting of continuous cosine shaped lines and depressions.

40. A spectroscopic rotating compensator material system investigation system as in claim 32, in which the dispersive optics comprises a prism.

41. A spectroscopic rotating compensator material system investigation system as in claim 40 which further comprises a focusing element after said stage for supporting a material system and prior to said dispersive optics.

42. A spectroscopic rotating compensator material system investigation system as in claim 32 in which compensators are present both before and after said stage for supporting a material system, and a selection from the group consisting of:

both said compensators are caused to rotate in use; and one of said compensators is caused to rotate in use;

is made.

43. A spectroscopic rotating compensator material system investigation system as claim 32 which is characterized by a mathematical model comprising calibration parameters which are members of the group consisitng of:

polarizer azimuthal angle orientation;

present material system PSI;

present material system DELTA;

compensator azimuthal angle orientation(s);

retardance of said compensator(s);

analyzer azimuthal angle orientation; and detector system image persistance and read-out nonidealities;

which mathematical model is effectively a transfer function which enables calculation of electromagnetic beam intensity as a function of wavelength detected by a detector element, given intensity as a function of wavelength provided by said source of a polychromatic beam of electromagnetic radiation; said calibration parameters selected from the group consisting of:

polarizer azimuthal angle orientation;

present material system PSI;

present material system DELTA;

compensator azimuthal angle orientation(s);

retardance of said compensator(s);

analyzer azimuthal angle orientation; and detector system image persistance and read-out nonidealities;

being, in use, evaluated by performance of a mathematical regression of said mathematical model onto an at least two dimensional data set, said at least two dimensional data set being intensity values vs. wavelength and a parameter selected from the group of consisting of:

angle-of-incidence of said polychromatic beam of electromagnetic radiation with respect to a present material system; and azimuthal angle rotation of one element selected from the group consisting of:
said polarizer; and
said analyzer;

obtained over time, while at least on of said at least one compensator(s) is caused to continuously rotate.

* * * * *